United States Patent [19]

Lowe, III

[11] Patent Number: 5,451,586
[45] Date of Patent: Sep. 19, 1995

[54] 3-AMINO-2-ARYL QUINUCLIDINES

[75] Inventor: John A. Lowe, III, Stonington, Conn.

[73] Assignee: Pfizer Inc., New York, N.Y.

[21] Appl. No.: 955,733

[22] PCT Filed: Apr. 25, 1991

[86] PCT No.: PCT/US91/02853

§ 371 Date: Dec. 13, 1993

§ 102(e) Date: Dec. 13, 1993

[87] PCT Pub. No.: WO91/18899

PCT Pub. Date: Dec. 12, 1991

Related U.S. Application Data

[63] Continuation-in-part of Ser. No. 532,525, Jun. 1, 1990, abandoned.

[51] Int. Cl.[6] .................. C07D 453/02; A61K 31/435
[52] U.S. Cl. ..................... 514/305; 514/825; 514/826; 514/886; 514/887
[58] Field of Search ................ 546/133; 514/305, 825, 514/826, 886, 887

[56] References Cited

U.S. PATENT DOCUMENTS 3,560,510  2/1971  Warawa ............................. 514/17
5,162,339  11/1992  Lowe ................................ 546/133

FOREIGN PATENT DOCUMENTS

WO9109844  7/1991  WIPO .

OTHER PUBLICATIONS

Warawa et al., *J. Med. Chem.*, 18, 587 (1978).
Sandberg et al., *J. Med. Chem.*, 25, 1009 (1982).
Goadsby et al., *Ann. Neurol.*, 23, 193 (1988).
Sterling, "Quaternary and Tertiary Quinuclidines Derivatives . . . ", J. Pharm. Sci., vol. 80, No. 8, 1991 pp. 785-789.
Regoli et al., "Trends in Cluster Headache", edited by Sicuteri et al., Elsevier Scientific Publishers, Amsterdam, pp. 85-95 (1987).

*Primary Examiner*—Johann Richter
*Assistant Examiner*—Catherine S. Scalzo-Kilby
*Attorney, Agent, or Firm*—Peter C. Richardson; Paul H. Ginsburg; Grover F. Fuller, Jr.

[57] ABSTRACT

Compounds of the formula

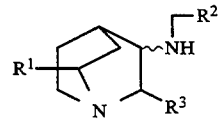

wherein $R^1$ is hydrogen or $(C_1-C_6)$alkyl; $R^2$ is phenyl, pyridyl, thienyl or furyl, and $R^2$ may optionally be substituted with from one to three substituents independently selected from $(C_1-C_4)$alkyl, $(C_1-C_4)$alkoxy, chloro, fluoro, bromo, iodo, and trifluoromethyl; $R^3$ is phenyl, naphthyl, pyridyl, thienyl or furyl, and $R^3$ may optionally be substituted with from one to three substituents independently selected from $(C_1-C_4)$alkyl, $(C_1-C_4)$alkoxy, chloro, fluoro, bromo, iodo and trifluoromethyl; and the pharmaceutically acceptable salts of such compounds.

These compounds are substance P antagonists and useful in the treatment of gastrointestinal disorders, inflammatory disorders, central nervous system disorders and pain.

10 Claims, No Drawings

3-AMINO-2-ARYL QUINUCLIDINES

This application is a CIP of 07/532525 filed Jun. 1, 1990, now abandoned, and a 371 of PCT/US91/02853.

BACKGROUND OF THE INVENTION

This invention relates to new quinuclidine derivatives and, in particular, to 3-amino-2-aryl quinuclidines. These compounds are substance P antagonists and are useful in the treatment of gastrointestinal disorders, inflammatory disorders, central nervous system disorders and pain.

U.S. Pat. No. 3,560,510 refers to certain 3-amino-2-benzhydrylquinuclidines as diuretic agents, and to the corresponding unsubstituted 3-benzylamino compounds as intermediates for preparing the same. E. J. Warawa et al., in *Journal of Medicinal Chemistry,* 18,587 (1975), refers to other members of the same series wherein the 3-amino moiety is either ethylamino, β-phenylethylamino, β-isopropylamino or 2-furfurylamino.

PCT Patent Application PCT/US 90/00116, assigned in common with the present application, refers to 3-amino piperidine derivatives and related compounds that are substance P antagonists useful in the treatment of inflammatory and central nervous system disorders.

PCT Patent Application PCT/US 88/04205, also assigned in common with the present invention, refers to cis-3-[(cyclic)methylamino]-2-[(α-substituted)arylmethyl]quinuclidines, 3-[(cyclic)methylamine]-2-[(α-substituted)arylmethyl]quinuclidines and cis-3-[(cyclic)methyleneamino]-2-[(α-substituted)arylmethyl]-quinuclidines that are substance P antagonists useful in the treatment of gastrointestinal disorders, central nervous system disorders, inflammatory diseases and pain.

Substance P is a naturally occurring undecapeptide belonging to the tachykinin family of peptides, the latter being so-named because of their prompt stimulatory action on smooth muscle tissue. More specifically, substance P is a pharmacologically active neuropeptide that is produced in mammals (having originally been isolated from gut) and possesses a characteristic amino acid sequence that is illustrated by D. F. Veber et al. in U.S. Pat. No. 4,680,283. The wide involvement of substance P and other tachykinins in the pathophysiology of numerous diseases has been amply demonstrated in the art. For instance, substance P has been shown to be involved in the transmission of pain (see B. E. B. Sandberg et al., *Journal of Medicinal Chemistry,* 25, 1009 (1982)), and more recently in the etiology of migraine and cluster headache (P. J. Gaddsby et al., *Ann. Neurol.,* 23, 193 (1988)), as well as in central nervous system disorders such as anxiety and schizophrenia, in respiratory and inflammatory diseases such as asthma and rheumatoid arthritis, respectively, and in gastrointestinal disorders such as ulcerative colitis and Crohn's disease, etc. (see D. Regoli in "Trends in Cluster Headache," edited by F. Sicuteri et al., Elsevier Scientific Publishers, Amsterdam, pp. 85–95, (1987)).

In the past, some attempts have been made to provide peptide-like substances that are antagonists for substance P and other tachykinin peptides in order to more effectively treat the various disorders and diseases listed above. The peptide-like nature of such substances make them too labile from a metabolic point of view to serve as practical therapeutic agents in the treatment of disease. The non-peptide antagonists of the present invention, on the other hand, do not possess this drawback.

SUMMARY OF THE INVENTION

The present invention relates to compounds of the formula

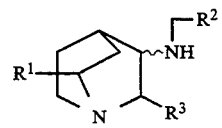

wherein $R^1$ is hydrogen or $(C_1-C_6)$alkyl; $R^2$ is phenyl, pyridyl, thienyl or furyl, and $R^2$ may optionally be substituted with from one to three substituents independently selected from $(C_1-C_4)$alkyl, $(C_1-C_4)$alkoxy, chloro, fluoro, bromo, iodo, and trifluoromethyl; $R^3$ is phenyl, naphthyl, pyridyl, thienyl or furyl, and $R^3$ may optionally be substituted with from one to three substituents independently selected from $(C_1-C_6)$alkyl, $(C_1-C_4)$alkoxy, chloro, fluoro, bromo, iodo and trifluoromethyl; and the pharmaceutically acceptable salts of such compounds.

Preferred compounds of the formula I are those wherein $R^2$ is 2-methoxyphenyl or 2,4-dimethoxyphenyl and $R^3$ is 3-chlorophenyl, 3-trifluoromethyl phenyl or phenyl. The enantiomers of these compounds having the 2S,3S absolute configuration are believed to be more active than the corresponding enantiomers having the 2R,3R absolute configuration.

Examples of specific compounds of the formula I are:

2-phenyl-N-((2-methoxy,5-fluorophenyl)methyl)-1-azabicyclo[2.2.2]octan-3-amine;

2-phenyl-N-((2-methoxy,5-chlorophenyl)methyl)-1-azabicyclo[2.2.2]octan-3-amine;

2-phenyl-N-((2-methoxy,4-fluorophenyl)methyl)-1-azabicyclo[2.2.2]octan-3-amine;

2-phenyl-N-((2-methoxy,4-chlorophenyl)methyl)-1-azabicyclo[2.2.2]octan-3-amine;

2-phenyl-N-((2,5-dimethoxyphenyl)methyl)-1-azabicyclo[2.2.2]octan-3-amine;

2-(2,4,6-trifluorophenyl)-N-((2-methoxyphenyl)methyl)-1-azabicyclo[2.2.2]octan-3-amine;

2-(2,4,6-trichlorophenyl)-N-((2-methoxyphenyl)methyl)-1-azabicyclo[2.2.2]octan-3-amine;

2-(3,5-dimethoxyphenyl)-N-((2-methoxyphenyl)methyl)-1-azabicyclo[2.2.2]octan-3-amine; and 2-(3,5-dichlorophenyl)-N-((2-methoxyphenyl)methyl)-1-azabicyclo[2.2.2]octan-3-amine.

This invention includes all stereoisomers of compounds of the formula I, including mixtures thereof.

This invention also includes all radiolabelled forms of the compounds of the formula I. The radiolabelled compounds of the formula I are useful as research and diagnostic tools in metabolism pharmacokinetic studies and in binding assays in both animal and man. Specific applications in research include radioligand binding assays, autoradiography studies and in vivo binding studies, while specific applications in the diagnostic area include studies of the substance P receptor in the human brain, such as up/down regulation in a disease state, and in vivo binding in the relevant tissues for inflammation, e.g., immune-type cells or cells that are directly involved in inflammatory bowel disorders and the like.

The present invention also relates to a pharmaceutical composition comprising a substance P antagonizing amount of a compound of the formula I, or a pharmaceutically acceptable salt thereof, and a pharmaceutically acceptable carrier.

The present invention also relates to a pharmaceutical composition comprising an amount of a compound of the formula I, or a pharmaceutically acceptable salt thereof, effective in the treatment of a disease mediated by an excess of substance P.

The present invention also relates to a pharmaceutical composition comprising an amount of a compound of the formula I, or a pharmaceutically acceptable salt thereof, effective in relieving or diminishing pain, or in the treatment of a disease selected from migraine, inflammatory disorders such as arthritis, psoriasis, inflammatory bowel disease and asthma, and central nervous system disorders such as anxiety-related disorders, schizophrenia and psychosis.

The present invention also relates to a method of antagonizing substance P in a mammal, including a human, comprising administering to said mammal a substance P antagonizing amount of a compound of the formula I, or a pharmaceutically acceptable salt thereof.

The present invention also relates to a method for treating a disease mediated by an excess of substance P in a mammal, including a human, comprising administering to a mammal in need of such treatment a substance P antagonizing amount of a compound of the formula I, or a pharmaceutically acceptable salt thereof.

The present invention also relates to a method of relieving or diminishing pain, or treating a disease selected from migraine, inflammatory disorders such as arthritis, psoriasis, inflammatory bowel disease and asthma, and central nervous system disorders such as anxiety-related disorders, schizophrenia and psychoses in a mammal, including a human, comprising administering to a mammal in pain or in need of such treatment a substance P antagonizing amount of a compound of the formula I, or a pharmaceutically acceptable salt thereof.

DETAILED DESCRIPTION OF THE INVENTION

The preparation of compounds of the formula I is illustrated in the following reaction scheme and discussed below. Unless otherwise indicated, in the reaction scheme and discussion that follow, $R^1$, $R^2$ and $R^3$ are defined as they are above.

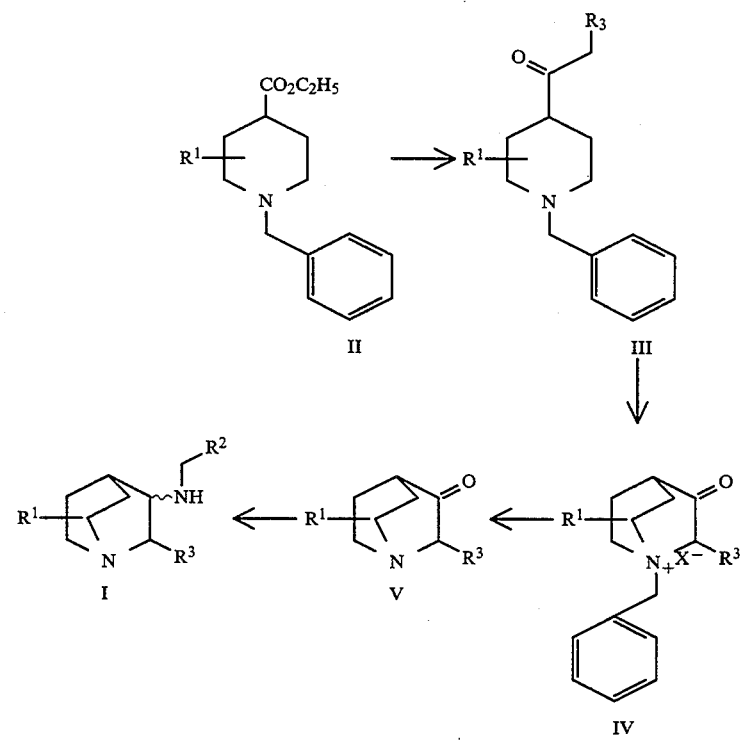

In a preferred embodiment, compounds of the formula I are prepared from compounds of the formula II as depicted in the above reaction scheme. Compounds of the formula II are known in the art and commercially available.

Referring to the reaction scheme, a compound of the formula II is reacted with a compound of the formula $R^3CN$, and the resulting reaction mixture is subjected to acidic hydrolysis to form a compound of the formula III. The reaction with $R^3CN$ is generally carried out in the presence of a base. Examples of suitable bases are organometallic bases such as butyl lithium, amide bases such as potassium hexamethyldisilazide and lithium diisopropylamide, and alkoxides such as potassium t-butoxide. The preferred base is potassium hexamethyldisilazide. Suitable acids for use in the hydrolysis step include strong mineral acids and related strong acids such as hydrochloric acid, sulfuric acid and acetic acid. A mixture of acetic and sulfuric acids is preferred. The reaction with $R^3CN$ is typically carried out in a reaction inert solvent such as hexane, benzene, toluene or an ethereal solvent, at a temperature from about −70° C. to about the reflux temperature of the solvent. The hydrolysis is usually conducted at a temperature from about room temperature to about the reflux temperature of the solvent.

The compound of the formula III so formed is then converted to the corresponding compound of the formula IV by reacting it first with bromine and then with a weak inorganic base. Examples of suitable inorganic bases include sodium carbonate, potassium carbonate and sodium bicarbonate. Sodium bicarbonate is preferred. In formula IV, the anion X− represents bromide, bicarbonate or another anion generated during the reaction of the compound of the formula III with bromine and a weak inorganic base. The reaction with bromine is typically conducted in a polar, reaction inert solvent such as acetic acid, tetrahydrofuran (THF), a lower alcohol or an ethereal solvent, at a temperature from about 15° C. to about the reflux temperature of the solvent. Preferably, the temperature is about 25° C. and the solvent is acetic acid. The subsequent base catalyzed cyclization is generally conducted in water or in a two phase system comprising water and a water immiscible inorganic solvent such as benzene, toluene, methylene chloride, hexane, or ether.

Hydrogenolysis of the resulting compound of the formula IV yields the corresponding compound of the formula V. The hydrogenolysis is generally conducted in a reaction inert solvent such as water, a lower alcohol, a chlorinated hydrocarbon, or an aromatic or ethereal solvent, in the presence of a catalyst. Noble metals (e.g. palladium, platinum, rhodium, etc.) and Raney Nickel are among the catalysts that may be used. The preferred solvent is ethanol and the preferred catalyst is palladium. The temperature may range from about −70° C. to about the reflux temperature of the solvent. Preferably it is about room temperature. The pressure may range from about 1.0 atmosphere to about 100 atmospheres, and is preferably about 3.0 atmospheres.

Alternatively, the compound of the formula IV may be reduced to form the corresponding compound of the formula V via a dissolving metal reduction. This is accomplished by dissolving the compound of formula IV in an appropriate solvent and then adding a metal. Examples of suitable metals are sodium, lithium, and potassium. Appropriate solvents include ammonia and lower alcohols. Preferably, the metal is sodium and the solvent is liquid ammonia. This reaction is generally carried out at a temperature from about −78° C. to about room temperature. The preferred temperature is about −78° C.

The above hydrogenolysis and reduction steps may result in the reduction of the ketone of the compound of formula IV to produce a compound identical to that of formula V except that the ketone has been converted to an alcohol. In such a case, the resulting alcoholic compound can be oxidized by methods known in the art to produce the corresponding ketone of formula V.

Compounds of the formula I are prepared from the corresponding compounds of the formula V by reacting the appropriate compound of the formula V with a compound of the formula $R^2CH_2NH_2$, and then reducing the product of such reaction. The reaction with $R^2CH_2NH_2$ is generally carried out in a reaction inert hydrocarbon, halogenated hydro- carbon, aromatic or ethereal solvent in the presence of a catalyst, at a temperature from about 15° C. to about the reflux temperature of the solvent. Suitable solvents include hexane, benzene, toluene, chloroform, methylene chloride, THF, ether and ethyl acetate. Toluene is preferred. The reaction temperature is preferably maintained between about room temperature and about the reflux temperature of the solvent. The catalyst may be an organic acid, a mineral acid, a polymer supported acid, a metal halide or molecular sieves. Examples of appropriate catalysts are titanium trichloride, titanium tetrachloride, camphor sulfonic acid and hydrogen chloride. Camphor sulfonic acid is preferred. For example, an appropriate catalyst for use with a more polar solvent is hydrogen chloride.

The reduction of the product of the foregoing reaction is typically carried out via hydrogenation or by using a metal hydride. The reaction with a metal hydride is typically conducted using borane methyl sulfide, sodium or lithium borohydride, triethylsilane or lithium aluminium hydride, preferably borane methyl sulfide. Suitable solvents for this reaction include reaction inert ethereal, hydrocarbon, aromatic or lower alcohol solvents. Examples of such suitable solvents include ethanol, THF, water, trifluoroacetic acid and acetic acid. The preferred solvent is THF. Reaction temperatures may range from about −70° C. to about the reflux temperature of the solvent. Preferably, the reaction is conducted at about the reflux temperature of the solvent.

The hydrogenation is generally conducted using a hydrogen gas pressure of from about 1 atmosphere to about 100 atmospheres, using a catalyst such as a noble metal (e.g., palladium, platinum, rhodium, etc.) or Raney Nickel. Appropriate reaction inert solvents for the hydrogenation step include water, lower alcohols and chlorinated hydrocarbons, as well as aromatic and ethereal solvents. Ethanol and ethyl acetate are preferred. The temperature may range from about −70° C. to about the reflux temperature of the solvent. Preferably, the pressure is about 3 atmospheres and the temperature is about room temperature.

The final product having the formula I may be released from any complexed metal or other residue by methods well known in the art.

The preferred compounds of the formula I may be resolved into their optically active forms by methods known to those skilled in the art. One such method is illustrated by the following sequence. A compound of formula I wherein $R^2$ is 4-methoxyphenyl is subjected to hydrolytic removal of the 4-methoxybenzyl group using a strong mineral acid such as hydrochloric, hydrobromic or hydroiodic acid, with hydrobromic acid being preferred, at a temperature from about room temperature to about the reflux temperature of the acid, with the reflux temperature being preferred. This reaction is usually conducted for about a period of about 2 hours. The resulting 2-aryl-1-azabicyclo[2.2.2]octan-3-amine compound is then resolved by converting it to a mixture of diastereomeric urea derivatives using the chiral isocyanate S-(+)-1-naphthylethylisocyanate, and separating the diastereomers by crystallization or chromatography.

The urea mixture is formed by heating the 2-aryl-1-azabicyclo[2.2.2]octan-3-amine in a reaction inert solvent such as an ethereal solvent or a hydrocarbon or halogenated hydrocarbon such as toluene, benzene, or hexane, at a temperature from about room temperature to about the reflux temperature of the solvent. It is preferable to carry out the reaction in toluene at the reflux temperature for about 4 hours. The resulting urea is then converted back to the desired 2-aryl-1-azabicyclo[2.2.2]octan-3-amine compound by reaction with strong acid such as a mineral acid, sulfuric acid or phosphoric acid, at a temperature from about 100° C. to about the reflux temperature of the acid. Preferably, sulfuric acid is used at the reflux temperature and the reaction is run for about 24 hours.

The desired —$CH_2R^2$ group is attached to the 2-aryl-1-azabicyclo[2.2.2]octan-3-amine compound to form the optically active compound of formula I by using the appropriate aldehyde of the formula $R^2$-CHO in the presence of a reducing agent such as a metal hydride or hydrogen and a noble metal catalyst. The reaction is generally carried out in a suitable solvent such as an alcohol, ethereal solvent, hydrocarbon or halogenated hydrocarbon for about 24 hours. Preferably, the metal hydride is sodium cyanoborohydride and the solvent is methanol. The temperature may range from about room temperature to about the reflux temperature of the solvent, with room temperature being preferred.

In each of the reactions discussed or illustrated above, pressure is not critical unless otherwise indicated. Pressures from about 0.5 atmospheres to about 5 atmospheres are generally acceptable, and ambient pressure, i.e. about 1 atmosphere, is preferred as a matter of convenience.

The majority of the compounds of the formula I are basic compounds and are capable of forming salts with various inorganic and organic acids. Although such salts must be pharmaceutically acceptable for administration to mammals, it is often desirable in practice to isolate the quinuclidine base compound from the reaction mixture as a pharmaceutically unacceptable salt, convert the latter back to the free base by treatment with an alkaline reagent, and then convert the free base to a pharmaceutically acceptable acid addition salt. The acid addition salts of the quinuclidine base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

The acids which may be used to prepare the pharmaceutically acceptable acid addition salts of the compounds of this invention are those which form non-toxic acid addition salts, i.e., salts containing pharmacologically acceptable anions, such as the hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)] salts.

The compounds of the formula I and their pharmaceutically acceptable salts exhibit significant substance P receptor-binding activity and therefore, are useful in the treatment of a wide variety of clinical conditions which are characterized of an excess of substance P activity. Such conditions include gastrointestinal disorders such as ulcer and colitis and other like diseases of the gastrointestinal tract, central nervous system disorders such as anxiety and psychosis, inflammatory diseases such as rheumatoid arthritis and inflammatory bowel diseases, respiratory diseases such as asthma, as well as pain in any of the aforesaid conditions, including migraine. These compounds are readily adapted to therapeutic use as substance P antagonists for the control and/or treatment of any of the above clinical conditions in mammals, including humans.

The compounds of the formula I, and their pharmaceutically acceptable salts may be administered orally, parenterally or topically. These compounds are most desirably administered in doses ranging from about 5.0 mg up to about 1500 mg per day, although variations will necessarily occur depending upon the weight and condition of the subject being treated and the particular route of administration chosen. A dosage level that is in the range of from about 0.07 mg to about 21 mg per kg of body weight per day is most desirable. Nevertheless, variations may still occur depending upon the species of animal being treated and its individual response to said medicament, as well as on the type of pharmaceutical formulation chosen and the time period and interval over which such administration is carried out. In some instances, dosage levels below the lower limit of the aforesaid range may be more than adequate, while in other cases still larger doses may be employed without causing any harmful side effects provided that such higher dose levels are first divided into several small doses for administration throughout the day.

The compounds of the present invention may be administered alone or in combination with pharmaceutically acceptable carriers or diluents by either of the three routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably at a pH 8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art.

Additionally, it is also possible to administer the compounds of the present invention topically when treating inflammatory conditions of the skin, and this may preferably be done by way of creams, jellies, gels, pastes, ointments and the like, in accordance with standard pharmaceutical practice.

The activity of the compounds of the present invention as substance P antagonists may be determined by their ability to inhibit the binding of substance P at its receptor sites in bovine caudate tissue, employing radioactive ligands to visualize the tachykinin receptors by means of autoradiography. The substance P antagonist activity of the herein described quinuclidine compounds may be evaluated by using the standard assay procedure described by M. A. Cascieri et al., as reported in the *Journal of Biological Chemistry*, 258, 5158 (1983). This method essentially involves determining the concentration of the individual compound required to reduce by 50% the amount of radiolabelled substance P ligands at their receptor sites in isolated cow tissues, thereby affording characteristic $IC_{50}$ values for each compound tested.

The anti-inflammatory activity of the compounds of the present invention may be demonstrated using the previously mentioned standard carrageenin-induced rat foot edema test. In this test, anti-inflammatory activity is determined as the percent inhibition of edema formation in the hind paw of male albino rats (weighing 150–190 g) in response to a sub-plantar injection of carrageenin. The carrageenin is injected as a 1% aqueous solution. Edema formation is then assessed by measuring the volume of the injected paw initially as well as three hours after the carrageenin injection. The increase in volume three hours after carrageenin injection constitutes the individual response. Compounds are considered active if the difference in response between the drug-treated animals (six rats/group) and a control group receiving the vehicle alone is significant on comparison with the results afforded by a standard compound like phenylbutazone at 33 mg/kg, via oral administration.

The anti-psychotic activity of the compounds of the present invention as neuroleptic agents for the control of various psychotic disorders may be determined primarily by a study of their ability to suppress substance P induced hypermotility in rats. This study is carried out by first dosing the rats with a control compound or with an appropriate test compound of the present invention, then injecting the rats with substance P by intracerebral administration via canula and measuring their individual locomotor response to said stimuli.

The following examples illustrate but do not limit the scope of the present invention.

EXAMPLE 1

4-((2-Cyano-2-phenyl)acetyl)-N-benzylpiperidine

To a 500 ml round-bottomed flask equipped with a condenser and a nitrogen inlet were added 10.26 ml (0.0889 mol) benzyl cyanide and 200 ml toluene. The solution was cooled to $-70°$ C., and 147.7 ml (0.0977 mol) of a 0.662 M solution of potassium hexamethyl disilazide in toluene was added dropwise over 5 minutes. The reaction was stirred at $-70°$ C. for 5 minutes, then at 0° C. for 30 minutes. There was then added a solution of 22 g (0.0889 mol) ethyl-N-benzylisonipecotate in 20 ml toluene. Stirring was continued at 0° C. for 1 hour, then at room temperature for 12 hr, and then at reflux for 3 hr. The reaction was cooled and poured onto ice, and then extracted with ethyl acetate. The solid that formed was collected and combined with the product resulting from chromatography of the ethyl acetate layer to afford 9.88 g (35%) of an oil.

$^1$H-NMR ($\delta$, CDCl$_3$): 1.6–3.1 (series of multiplets, 7H), 3.5 (m, 2H), 3.7 (m, 2H), 4.8 (m, 1H), 7.1–7.9 (m, 10H). IR (cm$^{-1}$, KBr): 2137, 2162 (CN). MS (%): 318 (25, parent), 202 (18), 146 (37), 91 (100), 42 (17).

EXAMPLE 2

4-(Phenylacetyl)-N-benzylpiperidine

To a 500 ml round-bottomed flask equipped with a condenser and a nitrogen inlet were added 9.88 g (31.1 mmol) 4-((2-cyano-2-phenyl)acetyl)-N-benzylpiperidine, 25 ml water, 50 ml acetic acid, and 50 ml concentrated sulfuric acid. The reaction was refluxed 3 hours, cooled, and poured into ice. The mixture was extracted into methylene chloride, dried and evaporated. The residue was chromatographed on silica gel with methylene chloride and ethyl acetate to afford 7.8 g (86%) of an oil. The oil was precipitated from ether with HCl to afford 8.2 g of a solid, mp 165°–167° C. (Spectra of free base):

$^1$H-NMR ($\delta$, CDCl$_3$): 1.6–1.8 (m, 4H), 1.9–2.1 (m, 2H), 2.45 (m, 1H), 2.91 (m, 2H), 3.50 (s, 2H), 3.73 (s, 2H), 7.1–7.4 (m 10H). IR (cm$^{-1}$, neat): 1706 (C=O). MS (%): 293 (39, parent), 202 (58), 146 (95), 91 (100), 65 (46).

EXAMPLE 3

2-phenyl-N-benzyl-1-[2.2.2]octan-3-one

To a 125 ml round-bottomed flask equipped with an addition funnel and a nitrogen inlet were added 4.0 g (12.1 mmol) 4-(phenylacetyl)-N-benzylpiperidine hydrochloride, 10 ml acetic acid, and dropwise 0.312 ml (12.1 mmol) bromine. The reaction was stirred at room temperature for 30 minutes and then evaporated to a reddish gum. The gum was dissolved in 100 ml methylene chloride, layered with aqueous sodium bicarbonate solution, and stirred at room temperature for 14 hours. The layers were separated and the aqueous layer evaporated. The residue was extracted with several portions of methylene chloride, and the organic layer evaporated to a white solid, mp 228°–230° C. The organic layer from the original separation was evaporated to recover the starting material, which was resubjected to the reaction to afford additional product, mp 228°–230° C. The yield was 665 mg (19%).

$^1$H-NMR ($\delta$, DMSO-d$_6$): 2.1–2.4 (m, 3H), 2.92 (m, 1H), 3.3–3.8 (m, 4H), 4.06 (m, 1H), 4.91 and 4.97 (singlets, 1H), 5.77 and 6.12 (singlets, 2H), 7.5–7.78 (m, 10H) IR (cm$^{-1}$, KBr): 1749 (C=O). MS (%): 292 (2, parent), 173 (44), 172 (55), 118 (20), 91 (100), 65 (17). Exact mass: calc'd for C$_{20}$H$_{22}$NO: 292.1701. Found: 292.1698.

EXAMPLE 4

2-Phenyl-1-azabicyclo[2.2.2]octan-3-one

A solution of 660 mg (2.26 mmol) 2-phenyl-N-benzyl-1-azabicyclo[2.2.2]octan-3-one in 100 ml ethanol was hydrogenated using 250 mg 10% palladium-on-carbon and 40 psi hydrogen for 1 hour. After filtration and evaporation, the residue was taken up in methylene chloride, washed with aqueous sodium bicarbonate solution, dried, and evaporated to give 320 mg (70%) of a yellow gum.

¹H-NMR ( , DMSO-d$_6$): 2.1–2.4 (m, 3H), 2.78 (m, 1H), 3.02 (m, 1H), 3.30 (m, 1H), 3.4–3.5 (m, 1H), 3.59 (m, 1H), 3.72 (m, 1H), 5.62 (s, 1H), 7.4–7.6 (m, 5H). IR (cm$^{-1}$, CHCl$_3$): 1726 (C=O). MS (%): 201 (1, parent), 173 (100), 172 (98), 144 (17), 118 (30), 91 (52).

EXAMPLE 5

2-Phenyl-N-(2-methoxyphenyl)methyl-1-azabicyclo-[2.2.2]octan-3-amine

To a 100 ml round-bottomed flask equipped with a Dean-Stark trap, condenser and a nitrogen inlet were added 1.4 g (6.96 mmol) 2-phenyl-azabicyclo[2.2.2]octan-3-one 1.36 ml (10.4 mmol) 2-methoxybenzylamine, 2 mg camphor- sulfonic acid, and 25 ml toluene. The reaction was refluxed with separation of water for 3 days, cooled, and evaporated. The residue was taken up in 30 ml dry tetrahydrofuran, and treated with 13 ml (25.9 mmol) of a 2.0 M solution of borane methyl sulfide in tetrahydrofuran. The reaction was refluxed 16 hours, cooled, and evaporated. The residue was taken up in 30 ml ethanol, treated with 2 g sodium carbonate and 2 g cesium fluoride, and refluxed 18 hours. The reaction was evaporated, taken up in water/methylene chloride, the layers separated, and the organic layer dried and evaporated. The residue was chromatographed on silica gel using methylene chloride and methanol as eluent to afford two product fractions, corresponding to the cis and trans isomers of the desired product, each of which was converted to the hydrochloride salt with HCl in ether.

Cis isomer: mp 262°–266° C., 5.7% yield. ¹H-NMR (δ, CDCl$_3$, free base): 1.31 (m, 1H), 1.59 (m, 1H), 1.72 (m, 1H), 1.91 (m, 1H), 2.20 (m, 1H), 2.8–3.0 (m, 3H), 3.11 (dd, J=4.6, 8.0, 1H), 3.26 (m, 1H), 3.65 (AB, J=13.7, 102, 2H), 3.74 (s, 3H), 4.10 (d, J=8.0, 1H), 6.7–7.4 (m, 9H). MS (%): 322 (27, parent), 201 (58), 121 (47), 91 (100). Exact mass, calc'd for C$_{21}$H$_{26}$N$_2$O: 322.2045. Found: 322.2039.

Anal. calc'd for C$_{21}$H$_{26}$N$_2$O·2HCl·1/4H$_2$O: C 63.08, H 7.18, N 7.00. Found: C 62.88, H 6.88, N 6.56.

Trans isomer: mp 293°–297° C., 17% yield. ¹H-NMR (δ, CDCl$_3$, free base): 1.41 (m, 2H), 1.64 (m, 1H), 1.8–2.0 (m, 3H), 2.62 (m, 2H), 2.98 (m, 1H), 3.04 (dd, J=1.7,6.7, 1H), 3.16 (m, 1H), 3.49 (d, J=6.7, 1H), 3.77 (s, 3H), 3.80 (AB, J=13.2,45.6, 2H), 6.8–7.4 (m, 9H). MS (%): 322 (18, parent), 201 (48), 121 (43), 91 (100). Exact mass, calc'd for C$_{21}$H$_{26}$N$_2$O: 322.2045. Found: 322.2047.

Anal. calc'd for C$_{21}$H$_{26}$N$_2$O·2HCl: C 63.79, H 7.13, N 7.08. Found: C 63.77, H 7.05, N 6.82.

EXAMPLE 6

Trans-2-phenyl-N-(phenylmethyl)-1-azabicyclo[2.2.2]-octan-3-amine

The title compound was prepared by a method analogous to that described above for preparing the cis isomer of Example 5. 8.5% yield, mp 270° C.

¹H-NMR (δ, CDCl$_3$, free base): 1.43 (m, 1H), 1.70 (m, 1H), 1.9–2.2 (m, 3H), 2.67 (m, 2H), 3.02 (m, 1H), 3.18 (m, 2H), 3.54 (d, J=7, 1H), 3.82 (AB, J=15, 33, 2H), 7.1–7.5 (m, 10H). MS (%): 292 (5, parent), 201 (51), 146 (42), 118 (21), 91 (100). Anal. calc'd for C$_{20}$H$_{24}$N$_2$O·2HCl·3/4H$_2$O: C 63.41, H 6.78, N 7.39. Found: C 63.81, H 7.00, N 6.89.

The title compounds of Examples 7–13 were prepared according to a procedure similar to that described in Example 1.

EXAMPLE 7

4-((2-Cyano-2-(1-naphthyl)acetyl)-N-benzylpiperidine

Prepared as a white solid, mp 130° C., 22.9% yield:

¹H-NMR (δ, CDCl$_3$): (enol form) 1.3–1.6 (m, 4H), 1.7–2.0 (m, 2H), 2.05 (m, 1H), 2.53 (m, 2H), 3.12 (broad s, 2H), 6.9–8.2 (multiplets, 12H).

IR (cm$^{-1}$, KBr): 2150 (CN).

MS (%): 368 (20, parent), 202 (50), 166 (40), 146 (60), 91 (100).

HRMS: Calc'd for C$_{25}$H$_{24}$N$_2$O: 368.1889. Found: 368.1854.

EXAMPLE 8

4-((2-Cyano-2-(3-chloro-phenyl)acetyl)-N-benzyl-piperidine

Prepared as a white solid, mp 130° C., 62% yield.

¹H-NMR (δ, DMSO-d$_6$): 1.4–1.7 (m, 4H), 1.91 (m, 2H), 2.70 (m, 1H), 2.82 (m, 2H), 3.42 (s, 2H), 5.75 (s, 1H), 6.64 (m, 1H), 7.01 (t, J=5, 1H), 7.2–7.4 (m, 5H), 7.52 (m, 1H), 8.24 (m, 1H).

IR (cm$^{-1}$ KBr): 2135 (CN)

MS (%): 352 (5.5, parent), 202 (13), 174 (11), 146 (39), 92 (11), 91 (100).

HRMS: Calc'd for C$_{21}$H$_{21}$N$_2$OCl: 352.1337. Found: 352.1327.

EXAMPLE 9

4-((2-Cyano-2-(3-trifluoromethyl-phenyl))acetyl)-N-benzylpiperidine

Prepared as a white solid, mp 224°–227° C., 25.6% yield:

¹H-M (δ, DMSO-d$_6$): (enol form) 1.7–2.0 (m, 4H), 2.9–3.1 (m, 3H), 3.3–3.5 (m, 2H), 4.29 (s, 2H), 6.98 (m, 1H), 7.26 (m, δ1H), 7.4–7.6 (m, 5H), 7.84 (m, 1H), 8.52 (m, 1H), 9.2–9.5 (broad, enol, 1H).

IR (cm$^{-1}$, KBr): 2140 (CN)

MS (%): 386 (50, parent), 202 (40), 146 (50), 91 (100).

HRS: Calc'd for C$_{22}$H$_{21}$N$_2$OF$_3$: 386.1606. Found: 386.1555.

EXAMPLE 10

4-((2-Cyano-2-(3-methoxy-phenyl))acetyl)-N-benzyl-piperidine

Prepared as a white solid, mp 201°–204° C., 26.8% yield:

¹H-NMR (δ, DMSO-d$_6$): (enol form) 1.7–2.0 (m, 4H), 2.8–3.1 (m, 3H), 3.32 (m, 2H), 3.68 ( s, 3H), 4.22 ( s, 2H), 6.33 (m, 1H), 6.98 (m, 1H), 7.27 (m, 1H), 7.4–7.6 (m, 5H), 7.73 (m, 1H).

IR (cm$^{-1}$, KBr ): 2160 (CN).

MS (%): 348 (12, parent), 202 (17), 173 (22), 146 (82), (100).

HRMS: Calc'd for C$_{22}$H$_{24}$N$_2$O$_2$: 348.1838. Found: 348.1837.

EXAMPLE 11

4-((2-Cyano-2-(4-methoxy-phenyl))acetyl)-N-benzyl-piperidine

Prepared as a white solid, mp 176°–179° C., quantitative yield:

¹H-NMR (δ, DMSO-d$_6$): (enol form) 1.7–2.0 (m, 4H), 2.71 (m, 2H), 2.98 (m, 1H), 3.25 (m, 2H), 3.73 ( s, 3H), 4.07 (broad s, 2H), 6.76 (m, 2H), 7.4–7.6 (m, 5H), 7.72 (m, 2H).

IR (cm$^{-1}$, KBr): 2160 (CN).

MS (%): 348 (80, parent), 202 (55), 174 (17), 146 (32), 91 (100).

HRMS: Calc'd for $C_{22}H_{24}N_2O_2$: 348.1838. Found: 348.1827.

EXAMPLE 12

4-((2-Cyano-2-(2-chloro-phenyl))acetyl)-N-benzyl-piperidine

Prepared as a white solid, mp 230°–232° C., 71.7 yield:

$^1$H-NMR ($\delta$, DMSO-d$_6$): (enol form) 1.7–2.0 (m, 4H), 2.8–3.0 (m, 2H), 3.2–3.5 (m, 3H), 3.98 (broad s, 2H), 7.0–7.6 (m, 9H).

IR (cm$^{-1}$, KBr): 2165 (CN).

MS (%): 352 (30), 202 (40), 146 (55), 91 (100).

EXAMPLE 13

4-((2-Cyano-2-(2-methoxy-phenyl))acetyl)-N-benzyl-piperidine

Prepared as a yellow gum, 100% yield:

$^1$H-NMR ($\delta$, CDCl$_3$): (enol form) 1.3–1.8 (m, 6H), 2.65 (m, 2H), 3.22 (s, 1H), 3.53 (s, 2H), 4.56 (s, 3H), 6.6–6.8 and 6.9–7.2 (multiplets, 9H).

IR (cm$^{-1}$, KBr): 2155 (CN).

MS (%): 348 (100, parent), 202 (35), 146 (40).

HRMS: Calc'd for $C_{22}H_{24}N_2O_2$: 348.1838. Found: 348.1823.

The title compounds of Examples 14–20 were prepared by a procedure similar to that described in Example 2.

EXAMPLE 14

4-((1-Naphthyl))acetyl)-N-benzylpiperidine

Prepared as a tan foam in 88.1% yield:

$^1$H-NMR ($\delta$, CDCl$_3$): 1.7–1.8 (m, 4H), 1.9–2.1 (m, 3H), 2.47 (m, 1H), 2.89 (m, 2H), 3.48 (s, 2H), 4.16 (s, 2H), 7.2–8.0 (m, 12H).

IR (cm$^{-1}$, KBr): 1718 (C=O).

MS (%): 343 (40, parent), 252 (40), 146 (50), 91 (100).

HRMS: Calc'd for $C_{24}H_{25}NO$: 343.1937. Found: 343.1813.

EXAMPLE 15

4-((3-Chloro-phenyl))acetyl)-N-benzylpiperidine

Prepared as an oil in 78.1% yield:

$^1$H-NMR ($\delta$, CDCl$_3$): 1.7–1.9 (m, 4H), 2.0–2.2 (m, 2H), 2.42 (m, 1H), 2.90 (m, 2H), 3.50 ( s, 2H), 3.72 ( s, 2H), 7.0–7.4 (m, 9H).

IR (cm$^{-1}$, KBr): 1712 (C=O).

MS (%): 327/329 (Cl$^{35}$/Cl$^{37}$, 15/5, parent), 236 (43), 146 (85), 91 (100).

HRMS: Calc'd for $C_{20}H_{22}NOCl^{35}$: 327.1390, Found: 327.1362.

EXAMPLE 16

4-((3-Trifluoromethyl-phenyl))acetyl)-N-benzyl-piperidine

Prepared as a yellow oil in 80.2% yield:

$^1$H-NMR ($\delta$, CDCl$_3$): 1.6–1.9 (m, 4H), 1.9–2.1 (m, 2H), 2.43 (m, 1H), 2.92 (m, 2H), 3.52 (s, 2H), 3.82 (s, 2H), 7.2–7.6 (m, 9H).

IR (cm$^{-1}$, KBr): 1711 (C=O).

MS (%): 361 (3.3, parent), 270 (21), 159 (14), 146 (80), 92 (11), 91 (100).

HRMS: Calc'd for $C_{21}H_{22}NOF_3$: 361.1648. Found: 361.1658.

EXAMPLE 17

4-((3-Methoxy-phenyl))acetyl)-N-benzylpiperidine

Prepared as a yellow oil in 85.2% yield:

$^1$H-NMR ($\delta$, CDCl$_3$): 1.6–1.9 (m, 4H), 1.9–2.1 (m, 2H), 2.43 (m, 1H), 2.91 (m, 2H), 3.47 (s, 2H), 3.72 (s, 2H), 3.80 (s, 3H), 6.7–6.9 and 7.2–7.4 (multiplets, 9H).

IR (cm$^{-1}$ KBr): 17 12 (C=O).

MS (%): 322 (1, parent-1), 174 (19), 173 (57), 172 (54), 146 (74), 92 (22), 91 (100), 82 (38).

HRMS: Calc'd for $C_{21}H_{25}NO_2$: 323.1883. Found: 323.1884.

EXAMPLE 18

4-((4-Methoxy-phenyl))acetyl)-N-benzylpiperidine

Prepared as a yellow solid, mp 80°–83° C., 55.4% yield:

$^1$H-NMR ($\delta$, CDCl$_3$): 1.7–1.9 (m, 4H), 1.9–2.1 (m, 2H), 2.43 (m, 1H), 2.92 (m, 2H), 3.50 (s, 2H), 3.69 (s, 2H), 3.79 (s, 3H), 6.84 (m, 2H), 7.11 (m, 2H), 7.2–7.4 (m, 5H).

IR (cm$^{-1}$, KBr): 1702 (C=O).

MS (%): 323 (100, parent), 232 (25), 146 (75), 121 (36)

HRMS: Calc'd for $C_{21}H_{25}NO_2$: 323.1883. Found: 323.1855.

EXAMPLE 19

4-((2-Chloro-phenyl))acetyl)-N-benzylpiperidine

Prepared as a white solid, mp 80°–83° C., 62.8 yield:

$^1$H-NMR ($\delta$, CDCl$_3$): 1.7–2.0 (m, 4H), 2.0–2.2 (m, 2H), 2.48 (m, 1H), 2.94 (m, 2H), 3.52 ( s, 2H), 3.88 ( s, 2H), 7.1–7.5 (m, 9H).

IR (cm$^{-1}$, KBr): 1710 (C=O).

MS (%): 327 (44, parent), 236 (80), 146 (100).

HRMS: Calc'd for $C_{20}H_{22}ONCl^{35}$: 327.1389. Found: 327.1360.

EXAMPLE 20

4-((2-Methoxy-phenyl))acetyl)-N-benzylpiperidine

Prepared as a yellow oil in 62.5% yield:

$^1$H-NMR ($\delta$, CDCl$_3$): 1.8–2.1 (m, 4H), 2.06 (s, 3H), 2.5–2.6 (m. 2H), 3.12 (m, 1H), 3.72 (AB, J=40, 65, 2H), 3.77 (s, 2H), 6.8–7.4 (m, 9H).

IR (cm.$^{-1}$, KBr): 1713 (C=O)

MS (%): 323 (60, parent), 232 (65), 146 (100).

HRMS: Calc'd for $C_{21}H_{25}NO_2$: 323.1883. Found: 323.1859.

The title compounds of Examples 21–27 were prepared by a procedure similar to that described in Example 3.

EXAMPLE 21

2-(1-Naphthyl)-N-benzyl-1-azabicyclo[2.2.2]octan-3-one

Prepared as a white solid, mp 162°–166° C., 59.9% yield:

$^1$H-NMR ($\delta$, CDCl$_3$): 1.80 (m, 2H), 2.21 (m, 1H), 2.43 (m, 1H), 2.63 (m, 2H), 3.01 (m, 1H), 3.43 (m, 3H), 3.78 (m, 1H), 5.93 (m, 1H), 7.2–8.1 and 9.51 (multiplets, 12H).

IR (cm$^{-1}$, KBr ): 1747 (C=O).

MS (%): 342 (5, parent), 223 (54), 222 (60), 172 (41), 146 (32), 141 (23), 92 (39), 91 (100), 82 (21), 65 (5e), 63 (29).

HRMS: Calc'd for $C_{24}H_{24}ONO$: 342.1858. Found: 342.1873.

EXAMPLE 22

2-(3-Chloro-phenyl)-N-benzyl-1-azabicyclo[2.2.2]-octan-3-one

Prepared as a white solid, mp 198°–200° C., 84.3% yield:

$^1$H-NMR (δ, DMSO-d$_6$): 2.1–2.4 (m, 2H), 2.92 (m, 1H), 3.3–3.6 (m, 4H), 3.69 (m, 1H), 3.84 (m, 1H), 4.02 (m, 1H 4.92 (m, 1H), 6.14 (s, 1H), 7.4–7.9 (m, 9H).

IR (cm$^{-1}$, KBr): 1741 (C=O).

MS (%): 326/328 (Cl$^{35}$/Cl$^{37}$, 8/2.7, parent), 209 (36), 208 (46), 207 (65), 206 (66), 172 (49), 170 (35), 127 (29), 92 (47), 91 (100), 90 (40), 63 (59).

HRMS: Calc'd for C$_{20}$H$_{21}$NOCl$^{35}$: 326.1311. Found: 326.1334.

EXAMPLE 23

2-(3-Trifluoromethyl-phenyl)-N-benzyl-1-azabicyclo-[2.2.2]octan-3-one

Prepared as a tan solid, mp 150°–155° C., 64.6% yield:

$^1$H-NMR (δ, CDCl$_3$): 2.22 (m, 1H), 2.3–2.6 (m, 3H), 3.06 (m, 1H), 3.26 (m, 1H), 3.4–3.6 (m, 4H), 5.64 (m, 1H), 6.18 (m, 1H), 7.4–7.9 and 8.47 (multiplets, 9H).

IR (cm$^{-1}$, KBr): 1748 (C=O).

MS (%): 360 (2.9, parent), 241 (45), 91 (100).

HRMS: Calc'd for C$_{21}$H$_{21}$NOF$_3$: 360.1576. Found: 360.1606.

EXAMPLE 24

2-(3-Methoxy-phenyl)-N-benzyl-1-azabicyclo-2.2.2]octan-3 -one

Prepared as a yellow foam in 46.6% yield:

$^1$H-NMR (δ, CDCl$_3$): 2.23 (m, 1H), 2.43 (m, 3H), 2.96 (m, 1H), 3.30 (m, 1H), 3.4–3.7 (m, 4H), 3.82 (s, 3H), 5.24 (m, 1H), 5.88 (m, 7.0–7.8 (m, 9H).

IR (cm$^{-1}$, KBr): 1742 (C=O).

MS (%): 322 (2.5, parent), 203 (100), 202 (82), 146 (20).

HRMS: Calc'd for C$_{21}$H$_{24}$NO$_2$: 322.1807. Found: 322.1832.

EXAMPLE 25

2-(4-Methoxy-phenyl)-N-benzyl-1-azabicyclo-[2.2.2]-octan-3-one

Prepared as a white solid, mp 210-213 ° C, in 38.2% yield:

$^1$H-NMR (δ, CDCl$_3$): 2.1–2.4 (m, 3H), 2.87 (m, 1H), 3.38 (s, 2H), 3.46 (m, 1H), 3.60 (m, 1H), 3.74 (m, 1H), 3.86 (s, 3H), 3.99 (m, 1H), 4.87 (m, 1H), 6.00 (s, 1H), 7.12 (m, 2H), 7.50 (m, 5H), 7.54 (m, 2H).

IR (cm$^{-1}$, KBr): 1742 (C=O).

MS (%): 322 (3, parent), 203 (36), 202 (37), 172 (17), 148 (12), 121 (16), 92 (10), 91 (100), 65 (13).

HRMS: Calc'd for C$_{21}$H$_{24}$NO$_2$: 322.1807. Found: 322.1805.

EXAMPLE 26

2-(2-Chloro-phenyl)-N-benzyl-1-azabicyclo-[2.2.2]-octan-3-one

Prepared as an amorphous solid in 46.9% yield:

$^1$H-NMR (δ, CDCl$_3$): 1.4–2.2 (m, 4H), 2.7–3.2 (m, 2H), 3.5–3.8 (m, 4H), 4.6–4.9 (m, 1H), 5.9–6.0 (m, 1H), 7.1–7.6 (m, 9H).

IR (cm$^{-1}$, KBr): 1742 (C=O).

MS (%): 326 (2.4, parent-Cl), 207 (15), 206 (16), 172 (17), 125 (22), 92 (16), 91 (100), 89 (21), 65 (29), 63 (17).

HRMS: Calc'd for C$_{20}$H$_{21}$NOCl$^{35}$: 326.1311. Found: 326.1302.

EXAMPLE 27

2- (2-Methoxy-phenyl)-N-benzyl-1-azabicyclo-[2.2.2]octan-3-one

Prepared as a yellow foam in 54.7% yield:

IR (cm$^{-1}$, KBr): 1749 (C=O).

$^1$H-NMR (δ, CDCl$_3$): 1.85 (m, 1H), 2.15 (m, 2H), 2.40 (m, 2H), 2.96 (m, 1H), 3.08 (m, 1H), 3.42 (s, 3H), 3.5–3.7 (m, 2H), 3.82 (m, 2H), 5.7–5.9 (m, 1H), 6.7–7.7 (m, 9H).

HRMS: Calc'd for C$_{21}$H$_{24}$NO$_2$: 322.1807. Found: 322.1773.

MS (%): 323 (33, parent), 232 (28), 203 (95), 202 (100), 172 (40), 146 (70), 134 (21), 119 (54).

The title compounds of Examples 28–34 were prepared by a procedure similar to that described in Example 4.

EXAMPLE 28

2-(1-Naphthyl)-1-azabicyclo[2.2.2]octan-3-one

Prepared as a white solid, mp 188°–190° C., 60.4 yield:

$^1$H-NMR (δ, CDCl$_3$): 2.06 (m, 1H), 2.17 (m, 3H), 2.70 (m, 1H), 2.80 (m, 2H), 3.38 (m, 2H), 6.03 (s, 1H), 7.24 (m, 1H), 7.40 (m, 1H), 7.53 (m, 2H), 7.85 (m, 2H), 8.11 (m, 1H).

IR (cm$^{-1}$, KBr): 1720 (C=O).

MS (%): 252 (67, parent, observed by FAB MS only), 223 (37, by FAB).

HRMS: Calc'd for C$_{16}$H$_{17}$N (parent-CO): 223.1357. Found: 223.1354.

EXAMPLE 29

2-(3-Chloro-phenyl)-1-azabicyclo[2.2.2]octan-3-one

Prepared as a yellow oil in 51.5% yield:

$^1$H-NMR (δ, CDCl$_3$): 1.96 (m, 2H), 2.13 (m, 2H), 2.59 (m, 1H), 2.82 (m, 2H), 3.22 (m, 2H), 4.32 (s, 1H), 7.2–7.5 (m, 4H).

IR (cm$^{-1}$, CHCl$_3$)): 1730 (C=O).

MS (%): 207 (100, parent-CO), 206 (72), 156 (37), 139 (57), 125 (38).

HRMS: Calc'd for C$_{20}$H$_{21}$NOCl$^{35}$: 326.1311. Found: 326.1334.

EXAMPLE 30

2-(3-Trifluoromethyl-phenyl)-1-azabicyclo[2.2.2]-octan-3-one

Prepared as a white solid, mp 220°–225° C., 96.4% yield:

$^1$H-NMR (δ, CDCl$_3$): 2.2–2.4 (m, 4H), 3.05 (m, 1H), 3.22 (m, 1H), 3.45 (m, 1H), 3.84 (m, 2H), 5.32 (m, 1H), 7.6–7.8 and 8.14 (multiplets, 4H).

IR (cm$^{-1}$, CHCl$_3$ )): 1755 (C=O).

MS (%): 270 (1.35, parent), 241 (100), 240 (42), 159 (35).

HRMS: Calc'd for C$_{14}$H$_{15}$NOF$_3$: 270.1097. Found: 270.0918.

EXAMPLE 31

2-(3-Methoxy-phenyl)-1-azabicyclo[2.2.2]octan-3-one

Prepared as a yellow oil in 40.7% yield:

$^1$H-NMR (δ, CDCl$_3$): 1.96 (m, 2H), 2.14 (m, 2H), 2.58 (m, 1H), 2.7–3.0 (m, 2H), 3.1–3.3 (m, 2H), 3.83 (s, 3H), 4.36 (s, 1H), 6.8–7.3 (multiplets, 4H).

IR (cm$^{-1}$, CHCl$_3$)): 1725 (C=O).

MS (%): 203 (100, parent-CO), 148 (18), 135 (23).

EXAMPLE 32

2-(4-Methoxy-phenyl)-1-azabicyclo[2.2.2]octan-3-one

Prepared as an amorphous solid in 84.1% yield:
$^1$H-NMR ($\delta$, CDCl$_3$): 1.95 (m, 2H), 2.10 (m, 2H), 2.58 (m, 1H), 2.7–3.0 (m, 2H), 3.1–3.3 (m, 2H), 3.79 (s, 3H), 4.32 (s, 1H), 6.86 (m, 2H), 7.28 (m, 2H).
IR (cm$^{-1}$, CHCl$_3$): 1720 (C=O).
MS (%): 203 (100), 202 (90), 148 (25), 121 (43).

EXAMPLE 33

2-(2-Chloro-phenyl)-1-azabicyclo[2.2.2]octan-3-one
Prepared as a yellow oil in quantitative yield:
$^1$H-NMR ($\delta$, CDCl$_3$): 2.1–2.5 (m, 4H), 2.99 and 3.05 (multiplets, 1H), 3.2–3.5 (m, 2H), 3.7–4.1 (m, 2H), 5.24 and 5.42 (singlets, 1H), 7.1–7.7 (m, 4H).
IR (cm$^{-1}$, KBr): 1739 (C=O).
MS (%): 207 (58, parent-CO), 206 (49), 173 (73), 172 (100), 125 (24), 91 (22).
HRMS: Calc'd for C$_{12}$H$_{14}$NCl$^{35}$ (parent - CO): 207.0846. Found: 207.0811.

EXAMPLE 34

2-(2-Methoxy-phenyl)-1-azabicyclo[2.2.2]octan-3-one
Prepared as a yellow solid, mp 129°–132° C., 29.0% yield:
$^1$H-NMR ($\delta$, CDCl$_3$): 2.0–2.2 (m, 4H), 2.61 (m, 1H), 2.7–3.3 (multiplets, 4H), 3.85 (s, 3H), 4.67 (s, 1H), 6.8–7.4 (m, 4H).
IR (cm$^{-1}$, KBr): 1717 (C=O).
MS (%): 232 (100, parent), 203 (50), 154 (28).
HRMS: Calc'd for C$_{14}$H$_{18}$NO$_2$: 232.1337. Found: 232.12776.

The title compound of Examples 35–43 were prepared by a procedure similar to that described in Examples 5 and 6.

EXAMPLE 35

2-(1-Naphthyl)-N-((2-methoxyphenyl)methyl)-1-azabicyclo [2.2.2]octan-3-amine

Only the cis isomer was obtained which was converted to its hydrochloride salt, mp 263° C., 44.3% yield:
$^1$H-NMR ($\delta$, CDCl$_3$): (free base), 1.4–1.9 (m, 3H), 2.14 (m, 1H), 2.58 (m, 1H), 2.9–3.1 (m, 2H), 3.4–3.5 (m, 2H), 3.62 (s, 3H), 3.73 (AB, J=20, 70, 2H), 4.24 and 4.56 (multiplets, 1H), 6.5–8.2 (multiplets, 11H).
MS (%): 372 (10, parent), 251 (100), 141 (56), 121 (80), 91 (65).
Anal. Calc'd for C$_{25}$H$_{28}$N$_2$O.2HCl.1/2H$_2$O: C 66.07, H 6.87, N 6.16. Found: C 65.92, H 6.45, N 6.08.

EXAMPLE 36

2-(1-Naphthyl)-N-((2-trifluoromethylphenyl)methyl)-1-azabicyclo[2.2.2]octan-3-amine Only the cis isomer was obtained, which was converted to its hydrochloride salt, mp 247°–250° C., 78.4% yield:
$^1$H-NMR ($\delta$, CDCl$_3$): (free base), 1.4–1.7 (m, 4H), 2.14 (m, 1H), 2.5–2.8 (m, 2H), 3.03 (m, 1H), 3.44 (m, 1H), 3.59 (m, 1H), 3.88 (dd, J=14, 30, 2H), 4.25 and 4.68 (multiplets, H), 7.1–8.2 (m, 11H).
MS (%): 410 (10, parent), 252 (32), 251 (100), 167 (30), 159 (69), 141 (69), 70 (35).
Anal. Calc'd for C$_{25}$H$_{25}$N$_2$F$_3$.2HCl.5/4H$_2$O: C 59.35, H 5.87, N 5.53. Found: C 59.37, H 5.42, N 5.52.

EXAMPLE 37

2-(3-Chloro-phenyl)-N-((2-methoxyphenyl)methyl)-1-azabicyclo[2.2.2]octan-3-amine Prepared each isomer as the hydrochloride salt: trans, mp 250°–255° C. (10.8% yield) and cis, mp 238°–240° C. (16.8% yield):
Trans isomer: $^1$H-NMR ($\delta$, CDCl$_3$): (free base), trans 1.40 (m, 1H), 1.6–1.8 (m, 2H), 2.00 (m, 1H), 2.09 (m, 1H), 2.60 (m, 2H), 2.96 (m, 2H), 3.13 (m, 1H), 3.43 (m, 1H), 3.82 (dd, J=15, 65, 2H), 3.83 (s, 3H), 6.8–6.9 and 7.1–7.4 (multiplets, 8H).
MS (%): 356 (13, parent), 235 (52) 176 (98), 121 (100), 91 (69).
Anal. Calc'd for C$_{21}$H$_{25}$N$_2$OCl.2HCl.1/2H$_2$O: C 57.48, H 6.43, N 6.31. Found: C 57.39, H 6.33, N 6.38.
Cis isomer: $^1$H-NMR ($\delta$, CDCl$_3$): (free base), cis 1.36 (m, 1H), 1.58 (m, 1H), 1.75 (m, 1H), 1.93 (m, 1H), 2.22 (m, 1H), 2.8–3.0 (m, 2H), 3.10 (m, 1H), 3.25 (m, 1H), 3.47 (m, 1H), 3.79 (s, 3H), 3.8–3.9 (m, 2H), 3.8 and 4.0 (m, 1H), 6.7–7.4 (m, 8H).
MS (%): 356 (8, parent), 235 (44), 176 (84), 136 (39), 125 (37), 121 (100), 91 (93), 70 (51), 65 (26).
Anal. Calc'd for C$_{21}$H$_{25}$N$_2$OCl.2HCl.3/4H$_2$O: C 56.89, H 6.47, N 6.31. Found: C 56.98, H 6.12, N 6.32.

EXAMPLE 38

2-(3-Trifluoromethyl-phenyl)-N-((2-methoxyphenyl)-methyl)-1-azabicyclo[2.2.2]octan-3-amine Prepared each isomer as the hydrochloride salt: trans, mp 243°–245° C. (27.9% yield) and cis, mp 211°–214° C. (7.1% yield):
Trans isomer: $^1$H-NMR ($\delta$, CDCl$_3$): (free base), trans 1.43 (m, 1H), 1.70 (m, 1H), 1.9–2.1 (m, 2H), 2.14 (m, 1H), 2.5–2.7 (m, 2H), 3.00 (m, 2H), 3.16 (m, 1H), 3.49 (m, 1H), 3.81 (s, 3H), 3.84 (dd, J=15, 55, 2H), 6.8–7.8 (m, 8H).
MS (%): 390 (2.6, parent), 176 (73), 159 (22), 121 (100), 70 (30).
Anal. Calc'd for C$_{22}$H$_{25}$N$_2$OF$_3$.2HCl: C 54.38, H 6.11, N 5.76. Found: C 54.41, H 5.34, N 5.51.
Cis isomer: $^1$H-NMR ($\delta$, CDCl$_3$): (free base), cis 1.38 (m, 1H), 1.5–1.8 (m, 3H), 1.93 (m, 1H), 2.26 (m, 1H), 2.8–3.0 (m, 2H), 3.1–3.3 (m, 2H), 3.67 (dd, J=15, 95, 2H), 3.76 (s, H), 4.11 (d, 1H), 6.8–7.6 (m, 8H).
MS (%): 390 (5.6, parent), 176 (71), 121 (100), 91 (65), 70 (23).
Anal. Calc'd for C$_{22}$H$_{25}$N$_2$OF$_3$.2HCl: C 54.38, H 6.11, N 5.76. Found: C 54.55, H 5.62, N 5.54.

EXAMPLE 39

2-(3-Methoxy-phenyl)-N-((2-methoxyphenyl)methyl)-1-azabicyclo[2.2.2]octan-3-amine Prepared each isomer as the hydrochloride salt: trans, mp 235°–238° C. (18.4% yield) and cis, amorphous (13.2% yield):
Trans isomer: $^1$H-NMR ($\delta$, CDCl$_3$): (free base), trans 1.41 (m, 1H), 1.68 (m, 1H), 1.8–2.0 (m, 2H), 2.08 (m, 1H), 2.64 (m, 2H), 2.9–3.1(m, 2H), 3.13 (m, 1H), 3.47 (m, 1H), 3.77 (s, 3H), 3.82 (s, 3H), 3.84 (dd, J=15, 45, 2H), 6.7–7.3 (m, 8H).
MS (%): 352 (22, parent), 231 (100), 176 (68), 121 (85), 91 (52).
Anal. Calc'd for C$_{22}$H$_{28}$N$_2$O$_2$.2HCl.1/2H$_2$O: C 60.83, H 7.07, N 6.44. Found: C 60.61, H 6.81, N 6.24.
Cis isomer: $^1$H-NMR ($\delta$, CDCl$_3$): (free base), cis 1.36 (m, 1H), 1.63 (m, 1H), 1.75 (m, 1H), 1.94 (m, 1H), 2.22 (m, 1H), 2.8–3.0 (m, 2H), 3.10 (m, 1H), 3.34 (m, 1H), 3.48 (m, 1H), 3.77 (s, 3H), 3.83 (s, 3H), 3.7–3.9 (m, 2H), 4.09 (m, 1H), 6.7–7.3 (m, 8H).

MS (%): 352 (20), 231 (90), 176 (50), 136 (49), 121 (100), 91 (79).

Anal. Calc'd for $C_{22}H_{28}N_2O_2 \cdot 2HCl \cdot 5/4H_2O$: C 58.99, H 7.31, N 6.25. Found: C 59.15, H 7.17, N 5.58.

EXAMPLE 40

2-(4-Methoxy-phenyl)-N-((2-methoxyphenyl)methyl-1-azbicyclo[2.2.2]octan-3-amine

Only the trans isomer was obtained, which was converted to its hydrochloride salt, mp 246°–250° C. (8.4% yield):

$^1$H-NMR ($\delta$, CDCl$_3$): (free base), 1.39 (m, 1H), 1.65 (m, 1H), 1.8–2.0 (m, 2H), 2.05 (m, 1H), 2.59 (m, 2H), 2.9–3.0 (m, 2H), 3.15 (m, 1H), 3.45 (m, 1H), 3.78 (s, 3H), 3.80 (s, 3H), 3.82 (dd, J=15, 45, 2H), 6.7–7.4 (m, 8H).

MS (%): 352 (7.5, parent), 176 (43), 121 (100), 91 (82), 70 (30).

Anal. Calc'd for $C_{22}H_{28}N_2O_2 \cdot 2HCl \cdot 1/4H_2O$: C 61.46, H 7.15, N 6.51. Found: C 61.35, H 7.03, N 6.49.

EXAMPLE 41

2-(2-Chloro-phenyl)-N-((2-methoxyphenyl)methyl)-1-azabicyclo[2.2.2]octan-3-amine Only the cis isomer was obtained, which was converted to its hydrochloride salt, mp 212° C.: $^1$H-NMR ($\delta$, CDCl$_3$): (free base), 1.38 (m, 1H), 1.6–1.9 (m, 2H), 1.94 (m, 1H), 2.13 and 2.22 (multiplets, 1H), 2.8–3.0 (m, 2H), 3.12 (m, 1H), 3.2–3.4 (m, 1H), 3.5 and 3.8 (m, 2H), 3.73 (s, 3H), 3.79 (m, 1H), 4.09 (m, 1H), 6.8–7.7 (m, 8H).

MS (%): 356 (3.8, parent), 322 (67), 237 (48), 202 (100), 201 (98), 176 (83), 121 (70).

Anal. Calc'd for $C_{21}H_{25}N_2OCl \cdot 1/2H_2O$: C 57.48, H 6.43, N 6.38. Found: C 57.86, H 6.45, N 5.83.

EXAMPLE 42

2-(2,Methoxy-phenyl)-N-((2-methoxyphenyl)-methyl)-1-azbicyclo[2.2.2]octan-3-amine-dihydrochloride trisesquihydrate Prepared as a white solid, mp 230° C., 10.3% yield: $^1$H-NMR ($\delta$CDCl$_3$): (free base), 1.35 (m, 1H), 1.5–2.1 (m, 3H), 2.21 (m, 1H), 2.9–3.1 (m, 2H), 3.27 (m, 1H), 3.4–3.5 (m, 1H), 3.59 (s, 3H), 3.72 (s, 3H), 3.8–4.0 (m, 3H), 4.13 (m, 1H), 6.7–7.5 (m, 8H).

IR (cm$^{-1}$, KBr): 1605, 1580.

MS (%): 352 (2, parent), 231 (100), 176 (33), 121 (99), 91 (75), 60 (32), 45 (39), 43 (48).

Anal. Calc'd for $C_{22}H_{28}N_2O_2 \cdot 2HCl \cdot 3/4H_2O$: C 60.20, H 7.22, N 6.38. Found: C 60.37, H 6.98, N 6.03.

EXAMPLE 43

2 -Phenyl-N-((3,4-dimethoxyphenyl)methyl)-1-azabicyclo [2.2.2]octan-3-amine

Prepared each isomer as the hydrochloride salt: trans, amorphous (14.1% yield) and cis, amorphous (17.5% yield):

Trans isomer: $^1$H-NMR ($\delta$, CDCl$_3$): trans 1.42 (m, 1H), 1.69 (m, 1H), 1.8–2.0 (m, 2H), 2.06 (m, 1H), 2.64 (m, 2H), 2.98 (m, 1H), 3.1–3.3 (m, 2H), 3.50 (m, 1H), 3.77 (dd, J=14, 35, 2H), 3.84 (s, 3H), 3.88 (s, 3H), 6.7–7.5 (m, 8H).

MS (%): 352 (3, parent), 201 (92), 151 (100), 70 (29).

Anal. Calc'd for $C_{22}H_{28}N_2O_2 \cdot 2HCL \cdot 3H_2O$: C 55.12, H 7.56, N 5.84. Found: C 54.75, H 7.09, N 5.67.

Cis isomer: $^1$H-NMR ($\delta$, CDCl$_3$): cis 1.36 (m, 1H), 1.67 (m, 1H), 1.78 (m, 1H), 1.93 (m, 1H), 2.14 (m, 1H), 2.9–3.1 (m, 2H), 3.20 (m, 1H), 3.32 (m, 1H), 3.58 (dd, J=18, 73, 2H), 3.83 (s, 3H), 3.85 (s, 3H), 3.9 (m, 1H), 4.17 (m, 1H), 6.6–7.4 (m, 8H).

MS (%): 352 (9.5, parent), 201 (99), 152 (22), 151 (100), 70 (38).

Anal. Calc'd for $C_{22}H_{28}N_2O_2 \cdot 2HCl \cdot 3H_2O$: C 55.12, H 7.56, N 5.84. Found: C 54.76, H 6.90, N 5.60.

The title compounds of Examples 44–46 were prepared by a method similar to that described in Example 1.

EXAMPLE 44

4 - ((2 -Cyano-2-(naphthyl)acetyl)-N-benzylpiperidine 52% yield, mp 200°–204° C.

$^1$H-NMR ($\delta$, CDCl$_3$): 1.65 (m, 1H), 1.9 (m, 2H), 2.1–2.2 (m, 1H), 2.42 (m, 1H), 3.2–3.4 (m, 4H), 3.6 (s, 2H), 7.0–8.2 (m, 12H).

IR (cm.$^{-1}$, KBR): 2140 (CN), 1640 (C=O).

MS (%): 368 (2, parent), 173 (42), 146 (62), 92 (31), 91 (100).

HRMS: Calc'd for $C_{25}H_{24}H_2O$: 368.1884. Found: 386.1886.

EXAMPLE 45

4-((2-Cyano-2-(2,4-difluorophenyl)acetyl)-N-benzylpiperidine

21% yield, mp 196°–199° C. $^1$H-NMR ($\delta$, CDCl$_3$): 1.8–2.4 (multiplets, 5H), 2.5–3.2 (multiplets, 4H), 3.68 (s, 2H), 7.2–7.5 (m, 8H).

IR (cm.$^{-1}$, KBr): 2178 (CN), 1620, 1600 (C=O).

MS (%): 354 (87, parent), 202 (69), 174 (32), 146 (100).

HRMS: Calc'd. for $C_{21}H_{20}N_2F_2O$: 354.1541. Found: 354.1536.

EXAMPLE 46

4-((2-Cyano-2-((4-phenyl)phenyl)acetyl)-N-benzylpiperidine

31% yield as a low melting solid.

$^1$H-NMR ($\delta$, CDCl$_3$): 1.5–1.8 (m, 4H), 1.95 (m, 1H), 2.6–3.0 (m, 4H), 3.33 (s, 2H), 7.0–7.9 (m, 14H).

$^{13}$C-NMR ($\delta$, CDCl$_3$): 39.6, 39.9, 40.2, 52.8, 126.1, 8.2, 128.6, 129.5 (remaining carbons not visible in this scan).

IR (cm.$^{-1}$, KBr): 2200 (CN).

HRMS: Calc'd. for $C_{27}H_{26}N_2O$: 394.2041. Found: 394.2053.

The title compound of Examples 47–49 were prepared by a procedure similar to that described in Example 2.

EXAMPLE 47

4- ((2-Naphthyl)acetyl)-N-benzylpiperidine $^1$H-NMR ($\delta$, CDCl$_3$): 1.6–1.8 (m, 4H), 1.96 (d of t, J=3, 11, 2H), 2.42 (m, 1H), 2.88 (m, 2H), 3.47 (s, 2H), 3.89 (s, 2H), 7.2–7.9 (m, 12H).

IR (cm. $^{-1}$, KBr): 1702 (C=O).

MS (%): 343 (85, parent), 252 (70), 172 (60), 146 (100).

HRMS: Calc'd. for $C_{24}H_{25}NO$: 343.1922. Found: 343.1929.

EXAMPLE 48

4-((2,4-Difluorophenyl)acetate)-N-benzylpiperidine

Yellow gum. $^1$H-NMR ($\delta$, CDCl$_3$): 1.7–1.9 (m, 4H), 2.02 (d of t, J=3, 11, 2H), 2.43 (m, 1H), 2.91 (m, 2H), 3.49 (s, 2H), 3.73 (s, 2H), 6.7–7.4 (m, 8H).

IR (cm.$^{-1}$, KBr): 1712 (C=O).

MS (%): 329 (28, parent), 238 (45), 146 (100).

HRMS: Calc'd. for $C_{20}H_{21}NF_2O$: 329.1588. Found: 329.1562.

EXAMPLE 49

4-(((4-Phenyl)phenyl)acetate)-N-benzylpiperidine 67% yield, mp 85°–90° C.

$^1$H-NMR ($\delta$, CDCl$_3$): 1.7–1.9 (m, 4H), 2.00 (d of t, J=3, 11, 2H), 2.46 (m, 1H), 2.93 (m, 2H), 3.50 (s, 2H), 3.78 (s, 2H), 7.2–7.7 (m, 14H).

$^{13}$C-NMR ($\delta$, CDCl$_3$): 27.9, 47.2, 48.2, 53.0, 63.2, 127.1, 127.3, 127.4, 128.2, 128.8, 129.1, 129.9, 133.2, 138.3, 139.9, 140.8, (not all carbons visible in this scan).

IR (cm.$^{-1}$, KBr): 1710 (C=O).

HRMS: Calc'd. for C$_{26}$H$_{27}$NO: 369.2088. Found: 369.2073.

The title compounds of Example 50–52 were prepared by a procedure similar to that described in Example 3.

EXAMPLE 50

2-(2-Naphthyl)-N-benzyl-1-azabicyclo[2.2.2]m octan-3-one 32% yield, oil.

$^1$H-NMR ($\delta$, CDCl$_3$): 2.20 (m, 1H), 2.40 (m, 1H), 2.5–2.6 (m, 2H), 3.03 (m, 1H), 3.29 (m, 1H), 3.49 (m, 2H), 3.61 (m, 1H), 5.28 (s, 1H), 5.57 (m, 1H), 6.05 (d, J=13, 1H), 7.3–8.4 (m, 12H).

IR (cm.$^{-1}$, KBr): 1745 (C=O).

MS (%): 342 (100, parent), 284 (3), 222 (5), 141 (7).

EXAMPLE 51

2-(2,4-Difluorophenyl)-N-benzyl-1-azabicyclo[2.2.2]-octan-3-one

31% yield, tan solid, m.p. 145° C.

IR (cm.$^{-1}$, KBr ): 1756 (C=O ).

MS (%): 328 (37, parent), 238 (35), 217 (67), 172 (41), 146 (100), 130 (92), 100 (65).

HRMS: Calc'd. for C$_{20}$H$_{20}$NOF$_2$: 328.1513. Found: 328.1484.

EXAMPLE 52

2-((4-Phenyl)phenyl)-N-benzyl-1-azabicyclo[2.2.2]-octan-3-one 56% yield as an oil.

$^1$H-NMR ($\delta$, CDCl$_3$): 2.21 (m, 1H), 2.4–2.6 (m, 3H), 3.00 (m, 1H), 3.31 (m, 1H), 3.56 (m, 3H), 5.36 (m, 1H), 5.93 (d, J=13, 1H), 7.1–8.0 (m, 14H).

IR (cm.$^{-1}$, KBr): 1750 (C=O).

MS (%): 368, (100, parent), 310 (3), 248 (6).

HRMS: Calc'd. for C$_{26}$H$_{26}$NO: 368.2010. Found: 368.1867.

The title compounds of Examples 53–55 were prepared by a procedure similar to that described in Example 4.

EXAMPLE 53

2-(2-Naphthyl)-1-azabicyclo[2.2.2 ]octan-3-one 41% yield, oil.

$^1$H-NMR ($\delta$, CDCl$_3$): 1.95 (m, 2H), 2.10 (m, 2H), 2.65 (m, 1H), 2.82 (m, 2H), 3.20 (m, 2), 4.55 (s, 1H), 7.4–8.0 (m, 7H).

$^{13}$C-NMR ($\delta$, CDCl$_3$): 24.3, 27.1, 40.8, 41.2, 48.6, 71.8, 126.10, 126.13, 126.5, 126.6, 127.5, 128.2, 128.3, (carbonyl carbon not visible in this scan)

IR (cm.$^{-1}$, CHCl$_3$): 1727 (C=O).

MS (%): 252 (1, parent +1), 251 (1, parent), 222 (100), 194 (45), 182 (52), 167 (60), 154 (56), 141 (55), 139 (51), 115 (40).

HRMS: Calc'd. for C$_{17}$H$_{17}$NO: 251. 1308. Found: 251.1308.

EXAMPLE 54

2- (2,4-Difluorophenyl)-1-azabicyclo[2.2.2]octan-3-one

79% yield, yellow gum.

$^1$H-NMR ($\delta$, CDCl$_3$): 1.4–1.9 (m, 2H), 2.09 (m, 2H), 2.61 (m, 1H), 2.84 (m, 2H), 3.21 (m, 2H), 4.50 (s, 1H), 6.7–7.3 (m, 3H).

IR (cm.$^{-1}$, CHCl$_3$): 1725 (C=O).

MS (%): 238 (100, parent +1), 208 (90).

HRMS: Calc'd. for C$_{13}$H$_{13}$NOF$_2$: 237.0957. Found: 237.09905.

EXAMPLE 55

2- ((4-Phenyl)phenyl)-N-benzyl-1-azabicyclo[2.2.2]-octan-3 -one

20% yield oil.

$^1$H-NMR ($\delta$, CDCl$_3$): 1.97 (m, 2H), 2.11 (m, 2H), 2.59 (m, 1H), 2.7–3.0 (m, 2H), 3.22 (m, 2H), 4.41 (s, 1H), 7.2–7.7 (m, 9H).

$^{13}$C-NMR ($\delta$, CDCl$_3$): 24.5, 26.8, 40.7, 41.2, 48.5, 72.5, 127.1, 127.2, 127.4, 128.7, 128.8, 134.6, (carbonyl carbon not visible in this scan).

IR (cm.$^{-1}$, KBr): 1725 (C=O)

MS. (%): 249 (100, parent-CO), 194 (20), 165 (30), 152 (17).

HRMS: Calc'd. for C$_{19}$H$_{19}$NO: 27.1464. Found 277.1461.

The title compounds of Examples 56–67 were prepared by a procedure analogous to that described in Example 5.

EXAMPLE 56

2-(2-Naphthyl)-N-((2-methoxyphenyl)methyl)-1-azabicyclo[2.2.2]octan-3-amine

Cis isomer: 24% yield.

$^1$H-NMR ($\delta$, CDCl$_3$): 1.37 (m, 1H), 1.66 (m, 1H), 1.77 (m, 1H), 1.80 (m, 1H), 2.22 (m, 1H), 3.00 (m, 2H), 3.23 (m, 1H), 3.3–3.4 (m, 1H), 3.4–3.8 (series of multiplets, 3H), 3.66 (s, 3H), 4.22 (m, 1H), 6.7–7.7 (m, 11H).

IR (cm. $^{-1}$, KBr): 1610 (C=C).

MS (%): 372 (8, parent), 251 (82), 176 (48), 141 (67), 112(100), 91(91).

HRMS: Calc'd. for C$_{25}$H$_{28}$N$_2$O: 372.2202. Found: 372.2199.

Trans isomer: 12% yield.

$^1$H-NMR ($\delta$, CDCl$_3$): 1.46 (m, 2H), 1.70 (m, 1H), 2.0–2.3 (m, 3H), 2.62 (t, J=7, 2H), 2.9–3.0 (m, 1H), 3.20 (m, 2H), 3.73 (s, 3H), 3.7–4.0 (m, 2H), 6.8–7.8 (m, 11H).

$^{13}$C-NMR ($\delta$, CDCl$_3$): 20.0, 25.5, 26.2, 41.7, 46.9, 49.8, 55.2, 58.2, 58.8, 67.0, 110,3, 120.5, 125.2, 125.6, 125.7, 127.0, 129.4, 127.8, 128.0, 128.4, 130.3.

IR (cm.$^{-1}$, KBr): 1610 (C=C).

MS (%): 372 (22, parent), 251 (100), 176 (55), 141 (60), 121 (74), 91 (75), 70 (41).

Anal. Calc'd. for C$_{25}$H$_{28}$NO$_2$.2HCl.0.5H$_2$O: C 66.07, H 6.87, N 6.16. Found: C 65.98, H 6.89, N 6.10.

EXAMPLE 57

2-(2,4-Difluorophenyl)-N-((2-methoxyphenyl)methyl)-1-azabicyclo[2.2.2]octan-3-amine Trans isomer. 12.5% yield.

$^1$H-NMR ($\delta$, CDCl$_3$): 1.4–1.6 (m, 2H), 1.67 (m, 1H), 1.81 (broad s, 1H, NH) 2.01 (m, 2H), 2.57 (m, 2H), 2.8–2.9 (m, 1H), 3.09 (m, 1H), 3.20 (m, 1H), 3.67 (s, 3H), 3.68 (dd, J=13, 37, 2H), 3.80 (m, 1H), 6.6–7.3 (m, 7H).

$^{13}$C-NMR (δ, CDCl$_3$): 19.6, 26.3, 26.4, 41.3, 47.2, 49.8, 55.0, 55.6, 61.0, 110.2, 120.3, 128.8, 130.0, (not all carbons visible in this scan).

IR (cm.$^{-1}$, KBr): 1610, 1602 (C=C)

MS (%): 358 (18), 237 (61), 217 (58), 176 (73), 154 (49), 136 (54), 127 (60), 121 (100), 91 (73), 70 (41).

Anal. Calc'd. for C$_{21}$H$_{24}$N$_2$OF$_2$.2HCl0.5H$_2$O: C 57.28, H 6.17, N 6.36. Found: C 57.24, H 6.19, N 6.26.

EXAMPLE 58

2-((4-Phenyl)phenyl)-N-((2-methoxyphenyl)methyl)-1-azabicyclo[2.2.2]octan-3-amine Trans isomer. 10% yield.

$^1$H-NMR (δ, CDCl$_3$): 1.38 (m, 1H), 1.64 (m, 1H), 1.78 (m, 1H), 1.97 (m, 1H), 2.23 (m, 1H), 2.98 (m, 3H), 3.16 (m, 1H), 3.51 (m, 1H), 3.5-3.8 (m, 2H), 3.75 (s, 3H), 4.14 (d, J=8, 1H), 6.8-7.8 (m, 13H).

$^{13}$C-NMR (δ, CDCl$_3$): 20.0, 24.9, 25.0, 43.9, 48.6, 49.4, 54.5, 55.0, 55.2, 62.0, 110.0, 110.2, 120.2, 120.4, 126.9, 127.0, 127.1, 127.8, 128.1, 128.2, 128.8, 129.9, 130.0, 137.9, 138.9, 141.1, 157.8.

IR (cm.$^{-1}$, KBr): 1602 (C=C)

MS (%): 398 (1, parent), 176 (52), 167 (57), 121 (100), 91 (78).

Anal. Calc'd. for C$_{27}$H$_{30}$N$_2$HCl.1.5H$_2$O: C 65.05, H 7.07, N 5.61. Found: C 64.93, H 6.94, N 5.41.

Cis isomer: 18% yield, mp 245°-248° C.

$^1$H-NMR (δ, CDCl$_3$): 1.44 (m, 2H), 1.70 (m, 1H), 21.0 (m, 2H), 2.67 (m, 2H), 3.02 (m, 1H), 3.10 (m, 1H), 3.19 (m, 1H), 3.54 (d, J=7, 1H), 3.80 (s, 3H), 3.8-4.0 (m, 2H), 6.7-7.7 (m, 13H).

$^{13}$C-NMR (δ, CDCl$_3$): 20.0, 25.5, 26.3, 41.8, 47.2, 48.7, 49.8, 55.2, 59.1, 66.8, 110.2, 110.3, 120.4, 120.5, 126.9, 127.07, 127.14, 128.0, 128.1, 128.4, 128.7, 129.8, 130.2, 139.6, 140.96, 141.03, 157.7.

IR (cm.$^{-1}$, KBr): 1602 (C=C)

MS (%): 398 (5, parent), 277 (64), 176 (44), 167 (63), 121 (100), 91 (90).

Anal. Calc'd. for C$_{27}$H$_{30}$N$_2$O.2HCl0.5H$_2$O: C 67.49, H 6.92, N 5.83. Found: C 67.20, H 7.02, N 5.64.

EXAMPLE 59

2-(3-Chlorophenyl)-N-((3-fluorophenyl)methyl)-1-azabicyclo[2.2.2]octan-3-amine

Trans isomer, 11% yield, mp 249°-252° C.

$^1$H-NMR (δ, CDCl$_3$): 1.36 (m, 1H), 1.61 (m, 1H), 1.75 (m, 1H), 1.85 (m, 1H), 2.12 (m, 1H), 2.92 (m, 3H), 3.18 (m, 2H), 3.63 (dd, J=14, 150, 2H), 4.07 (d, J=8, 1H), 6.8-7.6 (m, 8H).

IR (cm.$^{-1}$, KBr): 1604 (C=C).

MS (%): 344 (6, parent), 235 (68), 180 (39), 164 (57), 125 (33), 109 (100), 70 (44).

Anal. Calc'd. for C$_{20}$H$_{22}$N$_2$FCl.2HCl.0.25H$_2$O: C 56.89, H 85, N 6.55. Found: C 56.84, H 5.92, N 6.61.

EXAMPLE 60

2-(3-Chlorophenyl)-N-((2-chlorophenyl)methyl)-1-azabicyclo[2.2.2]octan-3-amine

Trans isomer, 16% yield, mp 236°-240° C.:

$^1$H-NMR (δ, CDCl$_3$): 1.34 (m, 1H), 1.60 (m, 1H), 1.73 (m, 1H), 1.89 (m, 1H), 2.24 (m, 1H), 2.9-3.1 (m, 3H), 3.1-3.3 (m, 2H), 3.73 (dd, J=7, 60, 2H), 4.05 (d, J=8, 1H), 7.1-7.5 (m, 8H).

IR (cm.$^{-1}$, KBr): 1587 (C=C)

MS (%): 360 (7, parent for Cl$^{35}$), 180/182 (82/31, Cl$^{35}$/Cl$^{37}$), 125/127 (100/49, Cl$^{35}$/Cl$^{37}$), 70 (49).

Cis isomer, 15% yield, mp 250°-253° C.:

$^1$H-NMR (δ, CDCl$_3$): 1.4 (m, 2H), 1.7 (m, 2H), 2.0 (m, 1H), 2.08 (m, 1H), 2.5-2.7 (m, 2H), 2.97 (m, 1H), 3.10 (m, 1H), 3.42 (d, J=6.7, 1H), 3.90 (dd J=7, 44, 2H), 7.1-7.5 (m, 8H).

IR (cm.$^{-1}$, KBr): 1587 (C=C)

MS (%): 360 (6, parent Cl$^{35}$), 235/237 (56/22, Cl$^{35}$/Cl$^{37}$), 180/182 (56/19, Cl$^{35}$/Cl$^{37}$) 125/127 (100/32 Cl$^{35}$/C$^{37}$) 70 (27).

Anal. Calc'd. for C$_{20}$H$_{22}$N$_2$Cl$_2$.2HCl.0.5H$_2$O: C 54.19, H 5.68, N 6.32. Found: C 54.32, H 5.40, N 6.28.

EXAMPLE 61

2-(3-Chlorophenyl)-N-((3-trifluoromethyl)methyl)-1-azabicyclo[2.2.2]octan-3-amine Trans isomer, 7% yield, mp 138°-142° C.

$^1$H-NMR (δ, CDCl$_3$): 1.36 (m, 1H), 1.61 (m, 1H), 1.76 (m, 1H), 1.85 (m, 1H), 2.12 (m, 1H), 2.93 (m, 3H), 3.18 (m, 2H), 3.69 (dd, J=14, 66, 2H), 4.09 (d, J=8, 1H), 7.0-7.6 (m, 8H).

IR (cm.$^{-1}$, KBr): 1578, 1598 (C=C).

MS (%): 394 (2, parent), 235 (71), 180 (49), 159 (100), 125 (38).

Anal. Calc'd. for C$_{21}$H$_{22}$N$_2$ClF$_3$.HCl.0.5H$_2$O: C 57.28, H 5.49, N 6.36. Found: C 57.03, H 5.03, N 6.38.

Cis isomer, 30% yield, mp 260-°264° C.

$^1$H-NMR (δ, CDCl$_3$): 1.44 (m, 2H), 1.69 (m, 1H), 1.89 (m, 1H), 2.06 (m, 1H), 2.61 (m, 2H), 2.88 (m, 1H), 2.98 (m, 1H), 3.16 (m, 1H), 3.44 (m, 1H), 3.87 (dd, J=14, 37, 2H), 7.2-7.7 (m, 8H).

IR (cm. $^{-1}$, KBr): 1578 (C=C)

MS (%): 394 (15, parent) 236 (97), 235 (100), 214 (60), 180 (76), 159 (95), 125 (78), 96 (63), 70 (77).

Anal. Calc'd. for C$_{21}$H$_{22}$N$_2$ClF$_3$.2HCl.2H$_2$O: C 50.06, H 5.60, N 5.56. Found: C 50.32, H 4.80, N 5.56.

EXAMPLE 62

2-(3-Chlorophenyl)-N-((2-methylphenyl)methyl)-1-azabicyclo[2.2.2 ]Octan-3-amine

Trans isomer, 9% yield, mp 236°-240° C.

$^1$H-NMR (δ, CDCl$_3$): 1.39 (m, 1H), 1.63 (m, 1H), 1.80 (m, 1H), 1.93 (m, 1H), 2.25 (m, 1H), 2.28 (s, 3H), 2.8-3.1 (m, 3H), 3.2-3.3 (m, 2H), 3.60 (dd, J=7, 67, 2H), 4.12 (d, J=8, 1H), 7.1-7.5 (m, 8H).

IR (cm.$^{-1}$, KBr): 1545 (C=C).

MS (%): 340 (12, parent), 235 (68), 160 (92), 105 (100), 70 (35).

Anal. Calc'd for C$_{21}$H$_{25}$N$_2$Cl·2HCl·1.25H$_2$O: C 57.81, H 6.80, N 6.42. Found: C 58.06, H 5.49, N 6.24.

Cis isomer, 27% yield, mp 248°-253° C.

$^1$H-NMR (δ, CDCl$_3$): 1.48 (m, 2H), 1.72 (m, 1H), 1.96 (m, 1H), 2.17 (m, 1H), 2.46 (s, 3H), 2.67 (m, 2H), 3.0-3.3 (m, 3H), 3.44 (m, 1H), 3.84 (dd, J=7, 53, 2H), 7.2-7.7 (m, 8H).

IR (cm,$^{-1}$, KBr): 1578 (C=C).

MS (%): 340 (15, parent), 235 (76), 160 (92), 105 (100), 70 (38).

Anal. Calc'd. for C$_{21}$H$_{25}$N$_2$Cl·2HCl·0.75H$_2$O: C 59.02, H 6.71, N 6.55. Found: C 59.19, H 6.27, N 6.47.

EXAMPLE 63

2-(3-Chlorophenyl)-N-((2-fluorophenyl)methyl)-1-azabicyclo[2.2.2]octan-3-amine

Trans isomer, 14% yield, mp 250°-255° C.

$^1$H-NMR (δ, CDCl$_3$): 1.36 (m, 1H), 1.5-1.8 (m, 2H), 1.88 (m, 1H), 2.17 (m, 1H), 2.8-3.0 (m, 3H), 3.14 (m, 2H), 3.70 (dd, J=6, 60, 2H), 4.06 (d, J=8, 1H), 7.0-7.5 (m, 8H).

IR (cm$^{-1}$, KBr): 1547 (C=C).
MS (%): 344 (5, parent), 235 (55), 164 (85), 125 (36), 109 (100), 70 (44).
Anal. Calc'd. for $C_{20}H_{22}FCl \cdot 2HCl \cdot 0.5H_2O$: C 56.28, H 5.90, N 6.56. Found: C 56.11, H 5.84, N 6.39.

Cis isomer, 24% yield, mp 259°–264° C.
$^1$H-NMR (δ, CDCl$_3$): 1.42 (m, 2H), 1.65 (m, 1H), 1.90 (m, 1H), 2.08 (m, 1H), 2.59 (m, 2H), 2.98 (m, 2H), 3.11 (m, 1H), 3.40 (m, 1H), 3.86 (dd, J=12, 36, 2H), 7.0–7.5 (m, 8H).
IR (cm.$^{-1}$, KBr): 1552 (C=C).
MS (%): 344 (7, parent), 235 (61), 164 (80), 125 (46), 109 (100), 70 (71).
Anal. Calc'd. for $C_{20}H_{22}N_2FCl \cdot 2HCl \cdot 0.5H_2O$: C 56.28, H 5.90, N 6.56. Found: C 56.07, H 5.78, N 6.14.

EXAMPLE 64

2-(3-Chlorophenyl)-N-((3-methylphenyl)methyl)-1-azabicyclo[2.2.2]octan-3-amine

Trans isomer, 15% yield, amorphous solid.
$^1$H-NMR (δ, CDCl$_3$): 1.35 (m, 1H), 1.62 (m, 1H), 1.75 (m, 1H), 1.89 (m, 1H), 2.15 (m, 1H), 2.33 (s, 3H), 2.8–3.1 (m, 3H), 3.2–3.3 (m, 2H), 3.66 (dd, J=13, 83, 2H), 4.07 (d, J=8, 1H), 6.9–7.5 (m, 8H).
IR (cm.$^{-1}$, KBr): 1578 (C=C).
MS (%): 340 (16, parent), 235 (74), 160 (94), 125 (48), 105 (100), 70 (71).
Anal. Calc'd. for $C_{21}H_{25}N_2Cl \cdot 2HCl \cdot H_2O$: C 58.41, H 6.76, N 6.48. Found: C 58.38, H 6.58, N 6.43.

Cis isomer, 13% yield, amorphous solid.
$^1$H-NMR (δ, CDCl$_3$): 1.42 (m, 2H), 1.67 (m, 1H), 1.90 (m, 1H), 2.07 (m, 1H), 2.34 (s, 3H), 2.59 (m, 2H), 3.00 (m, 2H), 3.12 (m, 1H), 3.43 (m, 1H), 3.77 (dd, J=13, 41, 2H), 7.0–7.5 (m, 8H).
IR (cm.$^{-1}$ KBr): 1579 (C=C).
MS (%): 340 (11, parent), 235 (63), 160 (93), 125 (27), 105 (1.00), 70 (49).
Anal. Calc'd. for $C_{21}H_{25}N_2Cl \cdot 2HCl \cdot 0.25H_2O$: C 60.22, H 6.62, N 6.69. Found: C 60.28, H 6.70, N 6.27.

EXAMPLE 65

2-(3-Chlorophenyl)-N-((2-trifluoromethylphenyl)methyl)-1-azabicyclo[2.2.2]octan-3-amine Cis isomer, 24% yield, mp 254°–258° C.
$^1$H-NMR (δ, CDCl$_3$): 1.44 (m, 2H), 1.67 (m, 1H), 1.91 (m, 1H), 2.02 (m, 1H), 2.62 (m, 2H), 3.01 (m, 3H), 3.41 (d, J=7, 1H), 3.95 (dd, J=13, 57, 2H), 7.2–7.7 (m, 8H).
IR (cm.$^{-1}$, KBr): 1579 (C=C).
MS (%): 394/396 (10/4, parent Cl$^{35}$/Cl$^{37}$), 235/237 (100/53, Cl$^{35}$/Cl$^{37}$), 159 (84), 125 (54), 96 (31), 70 (76).
Anal. Calc'd. for $C_{21}H_{22}N_2ClF_3 \cdot 2HCl \cdot 0.5H_2O$: C 52.90, H 5.28, N 5.87. Found: C 52.83, H 5.34, N 5.89.

EXAMPLE 66

2-(3-Chlorophenyl)-N-((2,4-dimethoxyphenyl)methyl)-1-azabicyclo[2.2.2]octan-3-amine Trans isomer, 8.0% yield, mp 210°–213° C.
$^1$H-NMR (δ, CDCl$_3$): 1.34 (m, 1H), 1.58 (m, 1H), 1.71 (m, 1H), 1.89 (m, 1H), 2.16 (m, 1H), 2.7–2.9 (m, 2H), 3.08 (m, 1H), 3.22 (m, 1H), 3.38 (m, 1H), 3.7–3.9 (m, 2H), 3.76 (s, 3H), 3.79 (s, 3H), 4.00 (d, J=8, 1H), 6.3–6.5 and 6.9–7.3 (m, 8 H).
IR (cm.$^{-1}$, KBr): 1618 (C=C).

MS (%): 386 (4, parent), 235 (52), 151 (100), 121 (56), 84 (60), 70 (61), 66 (71).
HRMS: Calc'd. for $C_{22}H_{27}N_2O_2Cl$: 386.1761. Found: 386.1759.
Anal. Calc'd. for $C_{22}H_{27}N_2O_2Cl \cdot 2HCl \cdot 0.25H_2O$: C 56.90, H 6.39, N 6.03. Found: C 56.75, H 7.76, N 5.33.

Cis isomer, 18.5% yield, mp 188°–192° C.
$^1$H-NMR (δ, CDCl$_3$): 1.2–1.4 (m, 2H), 1.68 (m, 1H), 1.95 (m, 1H), 2.04 (m, 1H), 2.55 (m, 1H), 2.91 (m, 2H), 3.09 (m, 1H), 3.4–3.5 (m, 2H), 3.71 (dd, J=13, 40, 2H), 3.78 (s, 3H), 3.80 (s, 3H), 6.3–6.5 and 7.0–7.3 (m, 8H).
IR (cm.$^{-1}$, KBr): 1618 (C=C).
MS (%): 386 (8, parent), 235 (37), 151 (54), 86 (100), 84 (99), 68 (72), 66 (97), 63 (46, 50 (50).
Anal. Calc'd. for $C_{22}H_{27}N_2O_2Cl \cdot 2HCl \cdot H_2O$: C 59.86, H 6.85, N 6.34. Found: C 59.73, H 6.83, N 6.03.

EXAMPLE 67

Cis-2-(3-chlorophenyl)-N-((4-methoxyphenyl)methyl)-1-azabicyclo[2.2.2]octan-3-amine Oil, 39% yield.
$^1$H-NMR (δ, CDCl$_3$): 1.37 (m, 1H), 1.53 (m, 1H), 1.70 (m, 1H), 1.84 (m, 1H), 2.14 (m, 1H), 2.8–3.0 (m, 2H), 3.1 (m, 1H), 3.455 (s, 2H), 3.62 (m, 1H), 3.69 (m, 1H), 3.77 (s, 3H), 4.08 (d, J=8, 1H), 6.8 and 7.0–7.2 (m, 8H).

I claim:

1. A compound of the formula

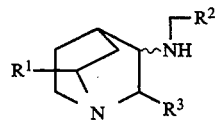

I wherein $R^1$ is hydrogen or ($C_1$–$C_6$)alkyl; $R^2$ is phenyl, pyridyl, thienyl or furyl, and $R^2$ may optionally be substituted with from one to three substituents independently selected from ($C_1$–$C_4$)alkyl, ($C_1$–$C_4$)alkoxy, chloro, fluoro, bromo, iodo, and trifluoromethyl; $R^3$ is phenyl, naphthyl, pyridyl, thienyl or furyl, and $R^3$ may optionally be substituted with from one to three substituents independently selected from ($C_1$–$C_4$)alkyl, ($C_1$–$C_4$)alkoxy, chloro, fluoro, bromo, iodo and trifluoromethyl; or a pharmaceutically acceptable salt of such compound.

2. A compound according to claim 1, wherein $R^2$ is 2-methoxyphenyl or 2,4-dimethoxyphenyl and $R^3$ is 3-chlorophenyl, 3-trifluoro-methylphenyl or phenyl.

3. A compound according to claim 2, wherein $R^2$ is 2-methoxyphenyl and $R^3$ is 3-chlorophenyl.

4. A compound according to claim 1, wherein said compound is selected from the group consisting of:
Trans-2-phenyl-N-(2-methoxyphenyl)methyl)-1-azabicyclo[2.2.2]octan-3-amine;
Cis-2-phenyl-N-(phenylmethyl)-1-azabicyclo[2.2.2]octan-3-amine;
2-(1-Naphthyl)-N-((2-methoxyphenyl)methyl)-1-azabicyclo[2.2.2]octan-3-amine;
2-(1-Naphthyl)-N-((2-trifluoromethylphenyl)-methyl)-1-azabicyclo[2.2.2]octan-3-amine;
2-(3-Chloro-phenyl)-N-((2-methoxyphenyl)-methyl)-1-azabicyclo[2.2.2]octan-3-amine;
Trans-2-(3-trifluoromethyl-phenyl)-N-((2-methoxyphenyl)methyl)-1-azabicyclo[2.2.2]octan-3-amine;
2-(3-Methoxy-phenyl)-N-((2-methoxyphenyl)-1-azabicyclo[2.2.2]octan-3-amine;

2-(4-Methoxy-phenyl)-N-((2-methoxyphenyl)-methyl)-1-azabicyclo[2.2.2]octan-3-amine;

2-(2-Chloro-phenyl)-N-((2-methoxyphenyl)-methyl)-1-azabicyclo[2.2.2]octan-3-amine;

2-(2-Methoxy-phenyl)-N-((2-methoxyphenyl)-methyl)-1-azabicyclo[2.2.2]octan-3-amine; and 2-Phenyl-N-((3,4-dimethoxyphenyl)methyl)-methyl)-1-azabicyclo[2.2.2]octan-3-amine.

5. A pharmaceutical composition comprising a substance P antagonizing amount of a compound according to claim 1 and a pharmaceutically acceptable carrier.

6. A pharmaceutical composition comprising an amount of a compound according to claim 1 effective in treating a disease mediated by an excess of substance P, and a pharmaceutically acceptable carrier.

7. A pharmaceutical composition comprising an amount of a compound according to claim 1 effective in relieving or diminishing pain, or in treating a disease selected from migraine, inflammatory disorders such as arthritis, psoriasis, inflammatory bowel disease and asthma, and central nervous system disorders such as anxiety-related disorders, schizophrenia and psychoses, and a pharmaceutically acceptable carrier.

8. A method of antagonizing substance P in a mammal, comprising administering to said mammal a substance P antagonizing amount of a compound according to claim 1.

9. A method for treating a disease mediated by an excess of substance P in a mammal, comprising administering to a mammal in need of such treatment a substance P antagonizing amount of a compound according to claim 1.

10. A method for relieving or diminishing pain, or treating a disease selected from migraine, inflammatory disorders such as arthritis, psoriasis, inflammatory bowel disease and asthma, and central nervous system disorders such as anxiety-related disorders, schizophrenia, and psychoses in a mammal, comprising administering to a mammal in pain or in need of such treatment a substance P antagonizing amount of a compound according to claim 1.

* * * * *